(12) United States Patent
Bollinger

(10) Patent No.: US 8,192,347 B2
(45) Date of Patent: Jun. 5, 2012

(54) ARTIFICIAL INSEMINATION

(75) Inventor: Stephen August Bollinger, Mansfield, MA (US)

(73) Assignee: Rinovum Women's Health, Inc., Pittsburgh, PA (US)

( * ) Notice: Subject to any disclaimer, the term of this patent is extended or adjusted under 35 U.S.C. 154(b) by 0 days.

(21) Appl. No.: 13/039,568

(22) Filed: Mar. 3, 2011

(65) Prior Publication Data

US 2011/0152606 A1 Jun. 23, 2011

Related U.S. Application Data

(63) Continuation of application No. PCT/US2010/035293, filed on May 18, 2010.

(60) Provisional application No. 61/179,222, filed on May 18, 2002.

(51) Int. Cl.
*A61D 7/00* (2006.01)

(52) U.S. Cl. .......................... 600/35; 128/844

(58) Field of Classification Search ............. 600/33–35; 604/346–353; 128/837–841, 844
See application file for complete search history.

(56) References Cited

U.S. PATENT DOCUMENTS

| | | | |
|---|---|---|---|
| 2,079,022 A | 5/1937 | Martin | |
| 2,141,040 A | 12/1938 | Holt | |
| 2,324,656 A | 7/1943 | Vincent | |
| 2,423,356 A | 7/1947 | Waterbury | |
| 2,764,975 A * | 10/1956 | Greenberg | 600/35 |
| 2,818,856 A | 1/1958 | Kohl | |
| 2,836,177 A | 5/1958 | Sells | |
| 2,855,932 A | 10/1958 | Stubbs | |
| 3,037,508 A | 6/1962 | Friedman | |
| 3,371,664 A | 3/1968 | Pleshette | |
| 3,404,682 A | 10/1968 | Waldron | |
| 3,683,904 A | 8/1972 | Forster | |
| 3,813,222 A | 5/1974 | La Vietes | |
| 3,872,869 A | 3/1975 | Randolph et al. | |
| 4,036,212 A | 7/1977 | Karuhn | |
| 4,198,965 A | 4/1980 | Strickman et al. | |
| 4,200,090 A | 4/1980 | Drobish | |
| 4,200,091 A | 4/1980 | Del Conte | |
| 4,219,016 A | 8/1980 | Drobish et al. | |
| 4,286,593 A | 9/1981 | Place et al. | |
| 4,300,544 A | 11/1981 | Rudel | |
| 4,304,226 A | 12/1981 | Drobish et al. | |
| 4,311,543 A | 1/1982 | Strickman et al. | |
| 4,320,751 A | 3/1982 | Loeb | |
| 4,356,259 A | 10/1982 | Banba | |
| 4,474,576 A | 10/1984 | Gobby | |
| 4,788,984 A | 12/1988 | Marsik | |
| 4,858,624 A | 8/1989 | Shihata | |

(Continued)

FOREIGN PATENT DOCUMENTS

WO 92/12687 A1 8/1992

(Continued)

*Primary Examiner* — Charles A Marmor, II
*Assistant Examiner* — Carrie R Dorna
(74) *Attorney, Agent, or Firm* — Scott E. Kamholz; Foley Hoag LLP

(57) ABSTRACT

An artificial insemination device may include a condom having a sheath and a reinforced cup that caps one end of the sheath, thereby having an inner concave surface and an outer convex surface; and a delivery handle comprising an elongate extension sized, shaped, shaped to contact the outer convex surface of the condom cup.

28 Claims, 26 Drawing Sheets

U.S. PATENT DOCUMENTS

| | | | |
|---|---|---|---|
| 4,993,432 | A | 2/1991 | Shields et al. |
| 5,358,847 | A | 10/1994 | Brown |
| 5,474,890 | A | 12/1995 | Di Virgilio et al. |
| 5,674,178 | A | 10/1997 | Root |
| 5,857,959 | A | 1/1999 | La Vean et al. |
| 6,027,443 | A | 2/2000 | Nag |
| 6,059,716 | A | 5/2000 | Lee et al. |
| 6,071,231 | A | 6/2000 | Mendoza et al. |
| 6,526,980 | B1 | 3/2003 | Tracy et al. |
| 6,699,226 | B2 | 3/2004 | Velazquez |
| 6,726,619 | B2 | 4/2004 | Gil Pascual |
| 6,796,973 | B1 | 9/2004 | Contente et al. |
| 6,923,185 | B1 | 8/2005 | Koch |
| D526,099 | S | 8/2006 | Tack |
| 7,165,550 | B1 | 1/2007 | Tracy et al. |
| 7,189,200 | B2 | 3/2007 | Chen |
| 7,241,261 | B2 | 7/2007 | Hladky |
| 7,344,492 | B2 | 3/2008 | Ainley, Jr. |
| 7,416,526 | B2 | 8/2008 | Chen |
| 7,419,465 | B2 | 9/2008 | Ainley, Jr. |
| 7,435,212 | B2 | 10/2008 | Chen |
| 7,458,931 | B2 | 12/2008 | Cassou |
| 2002/0133090 | A1 | 9/2002 | Michelle |
| 2007/0010705 | A1 | 1/2007 | Chen |
| 2007/0031895 | A1 | 2/2007 | Herr et al. |
| 2007/0238916 | A1 | 10/2007 | Chen |
| 2007/0256691 | A1 | 11/2007 | Ogram et al. |
| 2008/0242919 | A1 | 10/2008 | La Vean |

FOREIGN PATENT DOCUMENTS

| | | |
|---|---|---|
| WO | 96/06352 A1 | 2/1996 |

\* cited by examiner

Receptacle in extended position to receive Penis

Receptacle in retracted position, mated with delivery device

Receptacle in extended position to receive Penis

Delivery Device In retracted position 130
140
Delivery Device In extended position To connect to receptacle/Delivery device Delivery Device In active release position To release receptacle/Delivery device

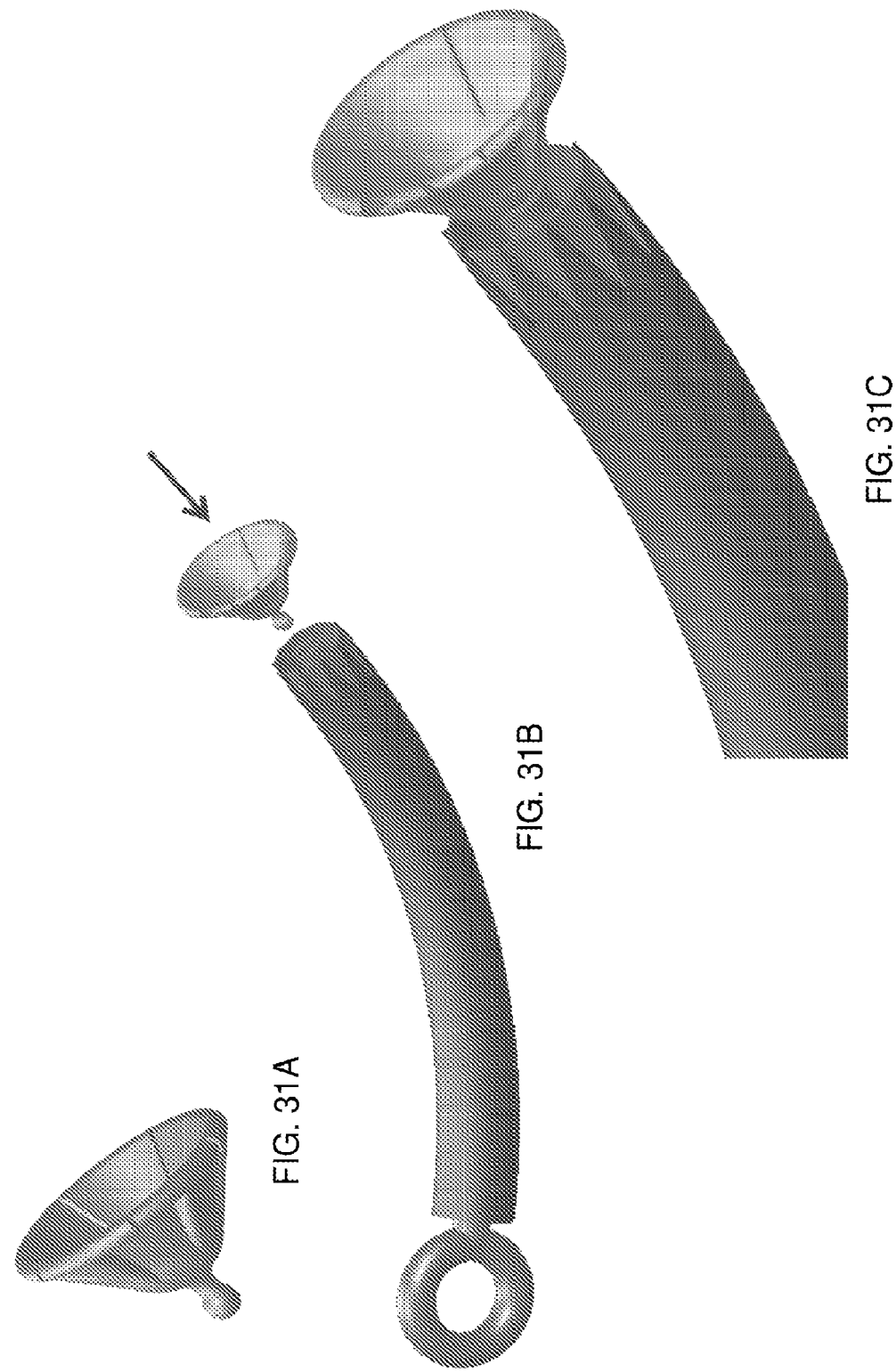

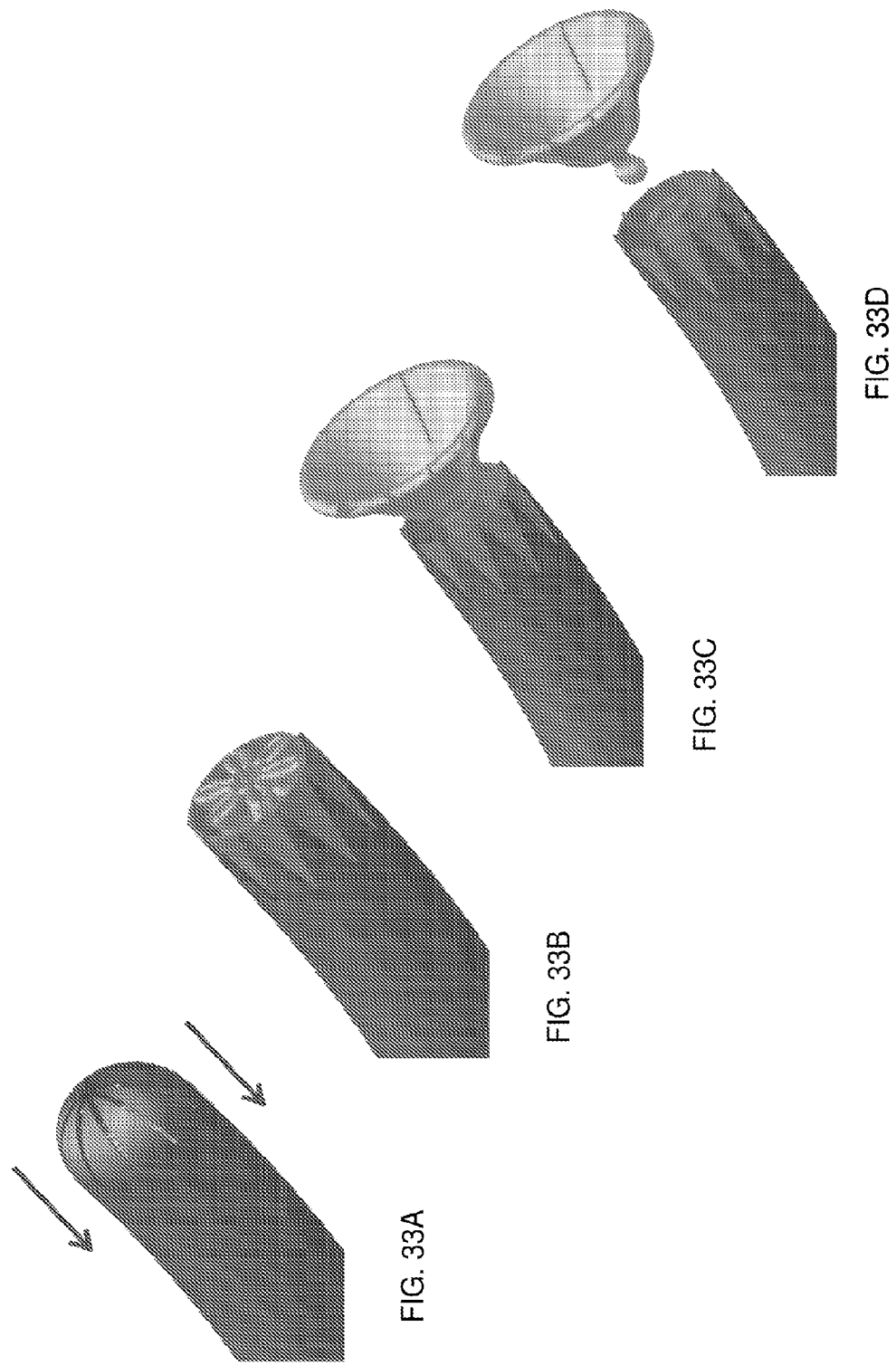

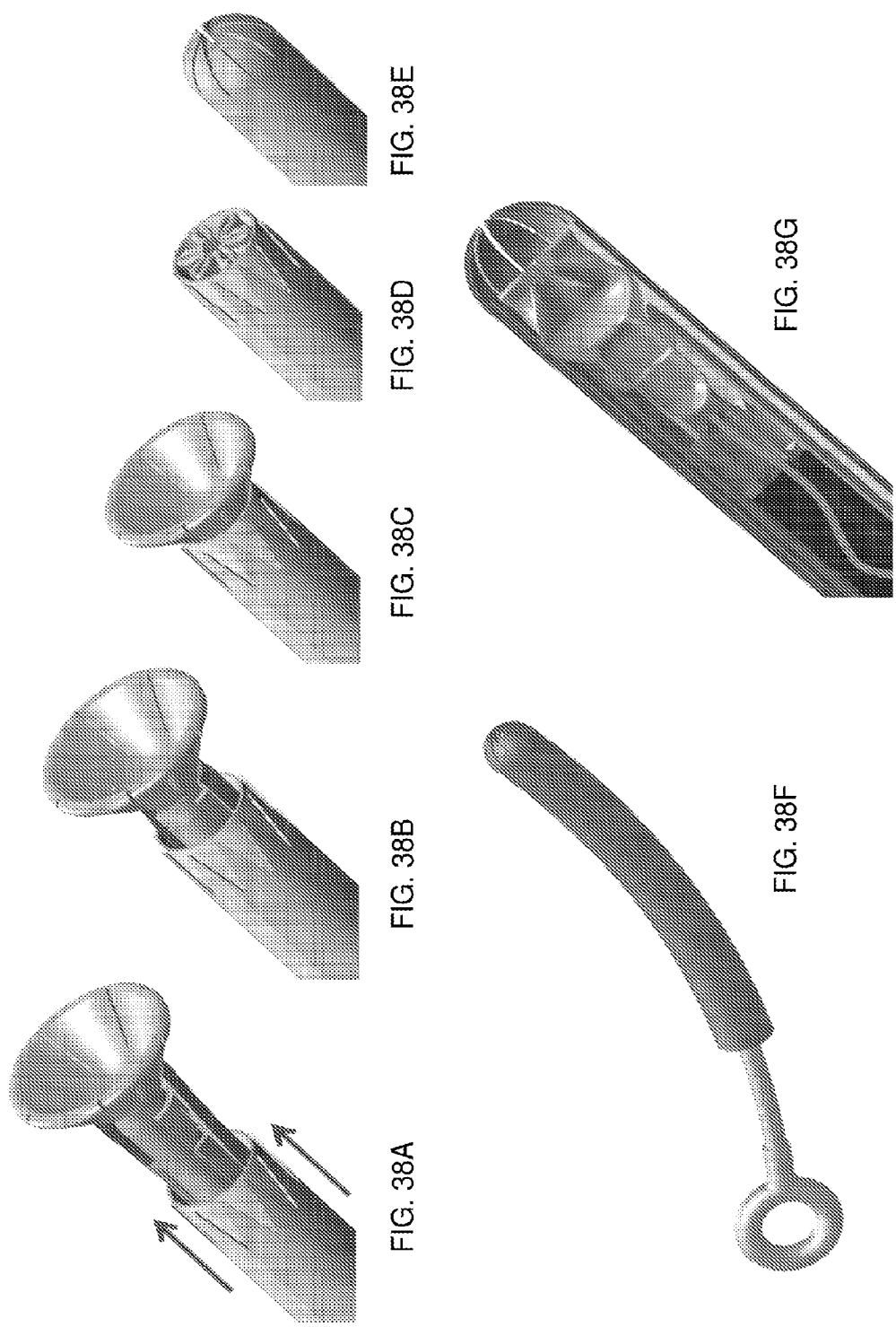

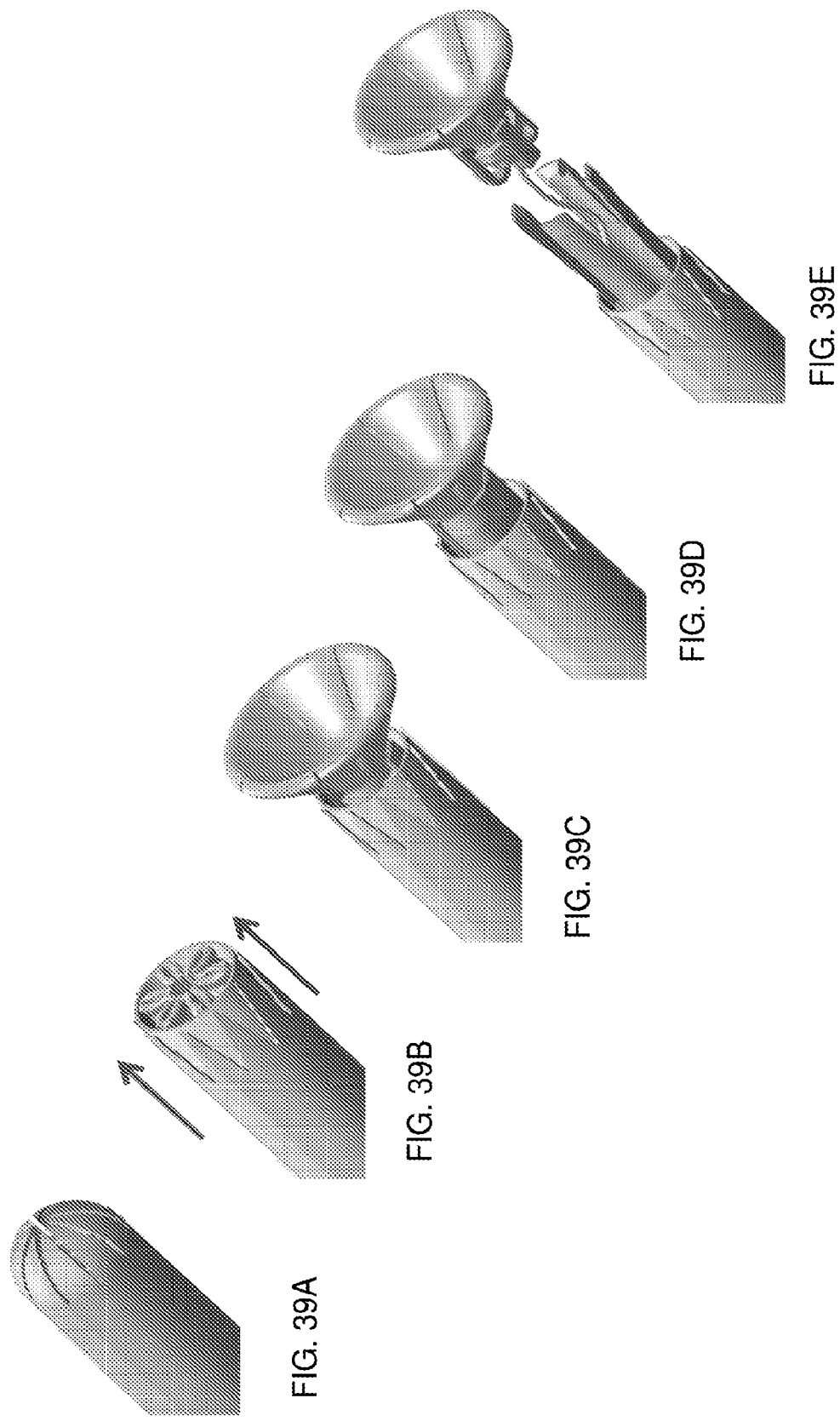

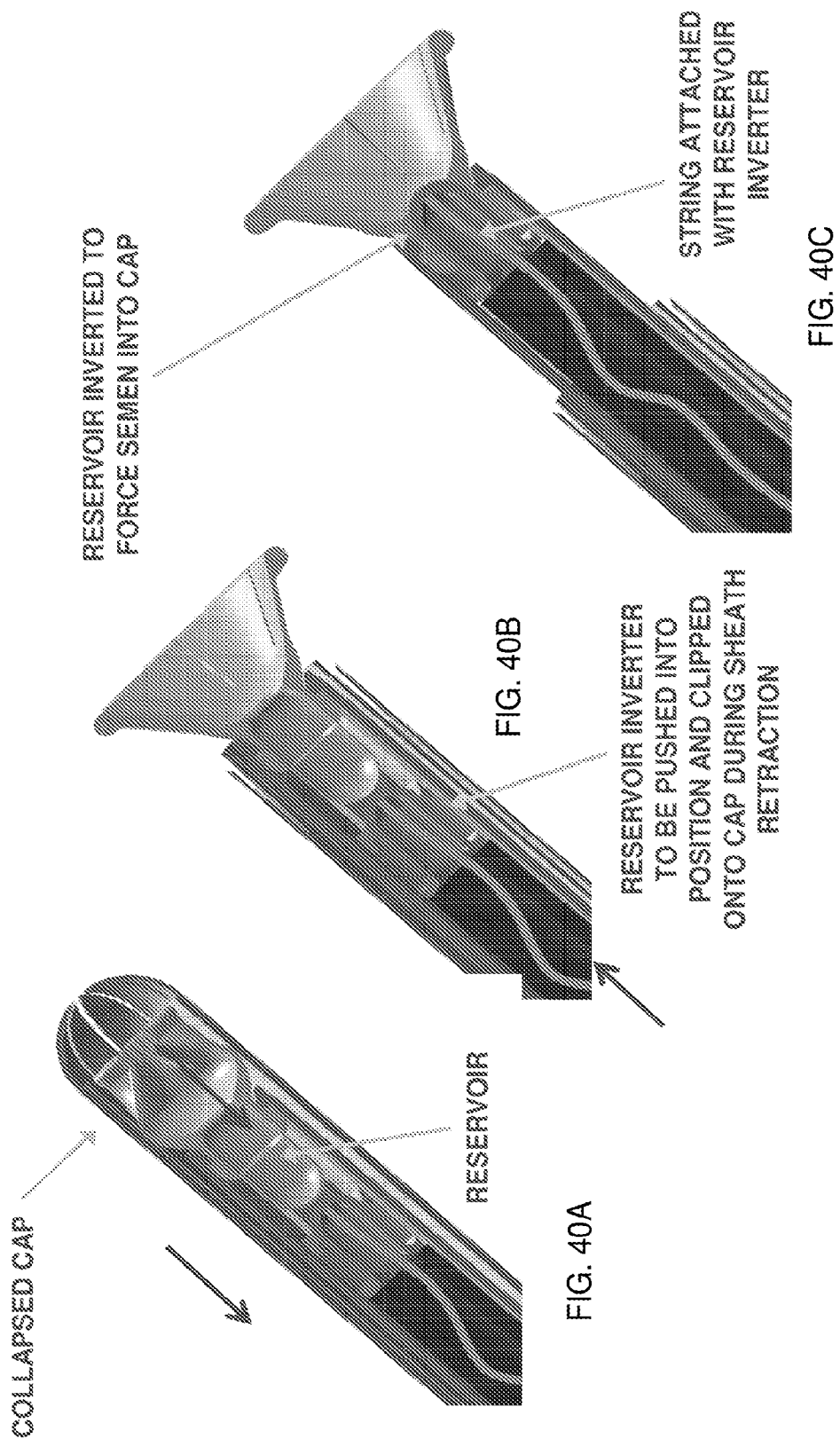

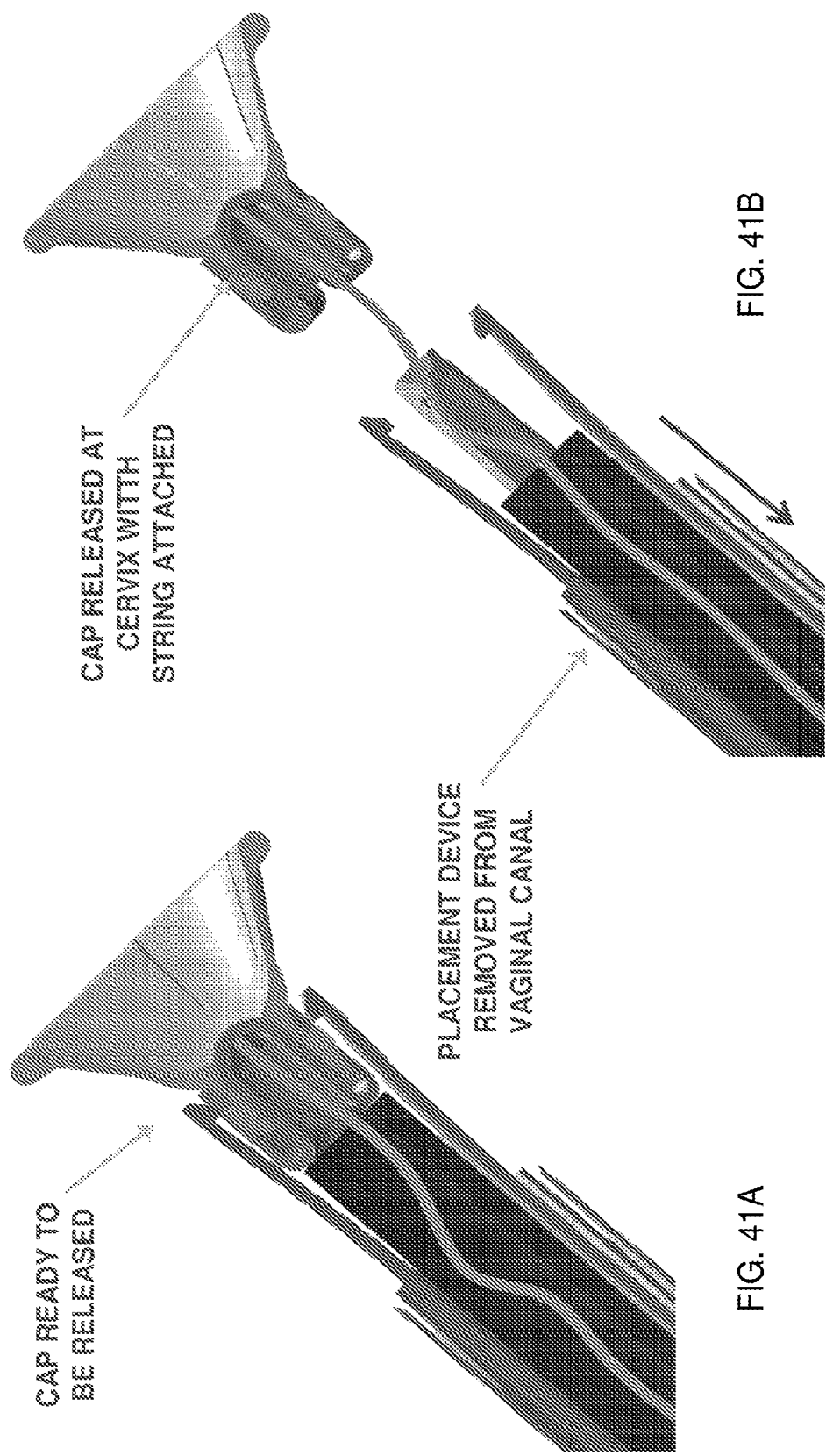

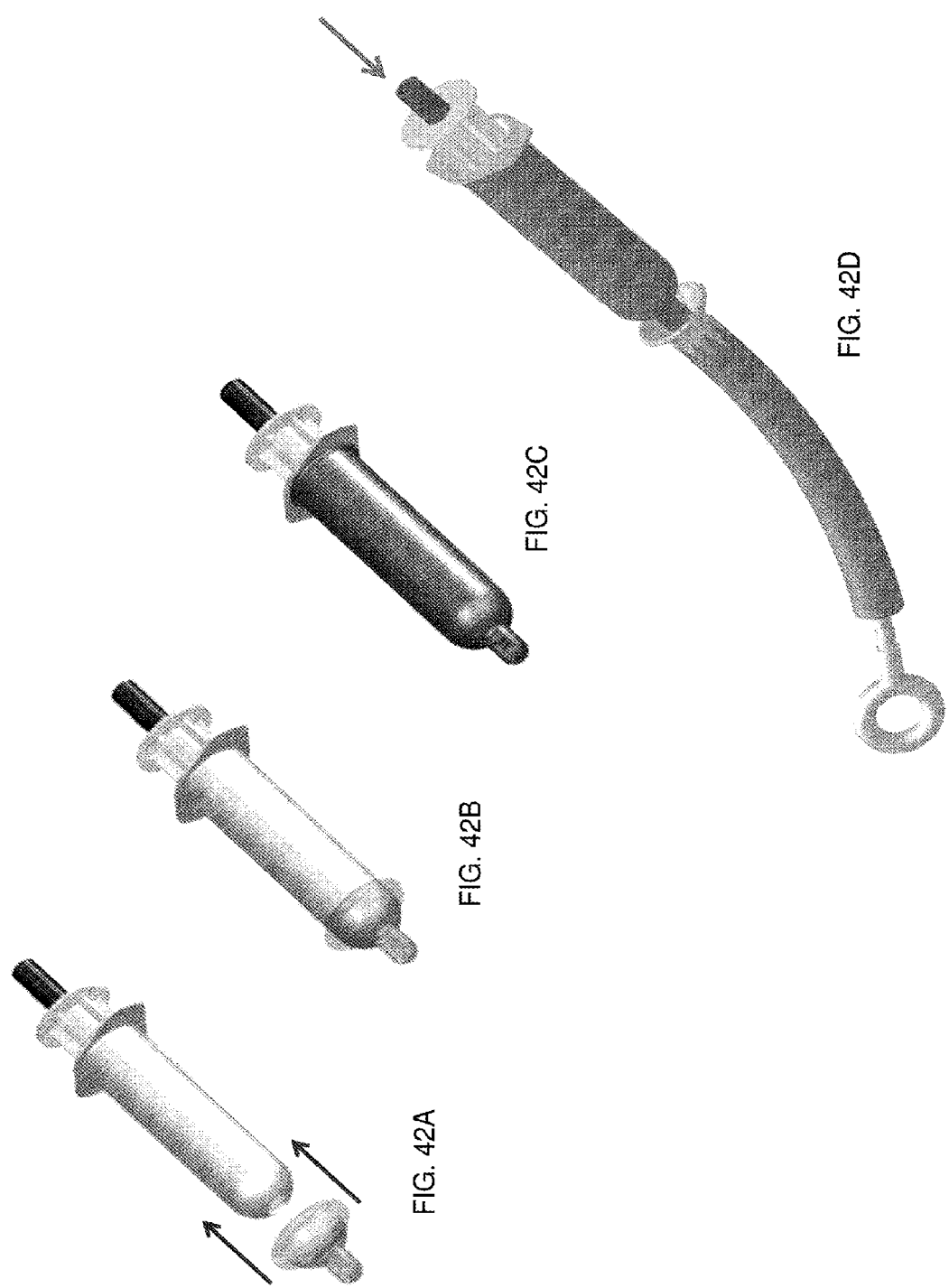

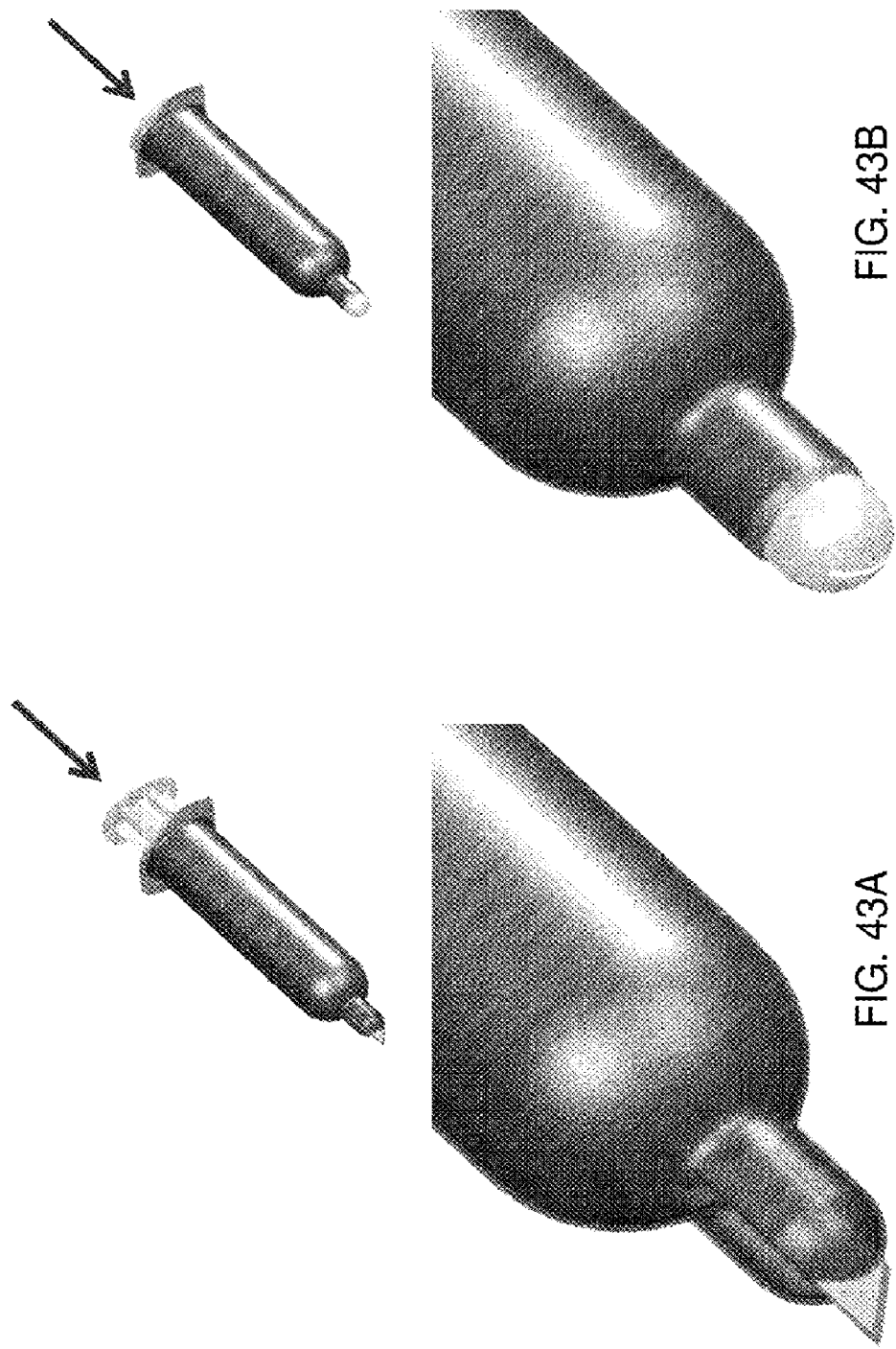

US 8,192,347 B2

ARTIFICIAL INSEMINATION

CROSS-REFERENCE TO RELATED APPLICATION

This application is a continuation of International application Ser. No. PCT/US2010/035293, filed May 18, 2010, which claims the benefit of U.S. provisional application Ser. No. 61/179,222, filed May 18, 2009, both of which are hereby incorporated herein by reference.

SUMMARY

An artificial insemination device may include a condom and a delivery handle. The condom may have a sheath and a reinforced cup that caps one end of the sheath (or may be inside of sheath). The cup thereby has an inner concave surface and an outer convex surface. The delivery handle may include an elongate extension sized and shaped to contact, interact, and/or connect to the outer convex surface of the condom cup.

The system may be used to carry out artificial insemination by collecting ejaculate in the cup of the condom, rolling the sheath down to the cup to form a supporting ring for the cup (or removing the sheath), contacting and or connecting the outer convex surface of the cup to the elongate extension of the delivery handle, advancing the cup and elongate extension to a cervix so that the ejaculate faces the cervix, withdrawing the elongate extension while leaving the cup at the cervix, and retrieving the cup after a delay.

BRIEF DESCRIPTION OF THE DRAWINGS

FIG. 31A shows an embodiment of a condom,
and FIGS. 31B-C show the condom with a handle.
FIGS. 32A-D and 33A-D show the condom of FIG. 31A with the handle.
FIGS. 37A-B, 38A-G, 39A-E, 40A-C, and 41A-B depict the reservoir condom and a handle.
FIGS. 42A-D and 43A-B depict a semen storage system.

DETAILED DESCRIPTION

The systems described herein may be used to facilitate artificial insemination. Artificial insemination ("AI"), sometimes termed "alternative insemination," is a process by which semen, containing live sperm, is introduced into a woman's reproductive tract in a way other than by sexual intercourse. It typically involves ejaculating into a vessel, transferring the ejaculate into an injector (such as a pipette or needle-less syringe), and delivering the ejaculate at or near a woman's cervix using the injector. (Sperm may also be deposited in the uterus but typically must be "washed" free of other components of seminal fluid) to avoid cramping, pain, and other side effects). The present systems improve AI by providing a condom into which a man ejaculates and then which can be immediately attached to a delivery handle to advancement to a woman's cervix. Alternatively, the condom and ejaculate may be temporarily stored in a storage system.

Figure 1:
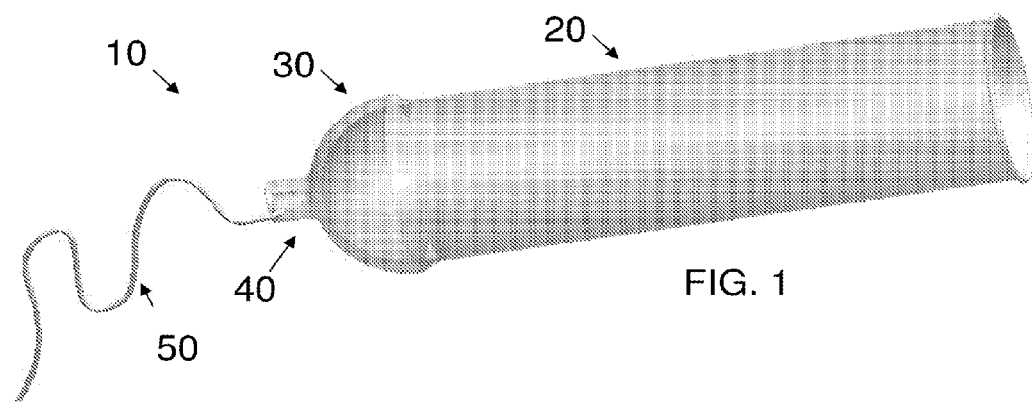
FIGS. 1-6 depict exemplary embodiments of condoms.
Figure 2:
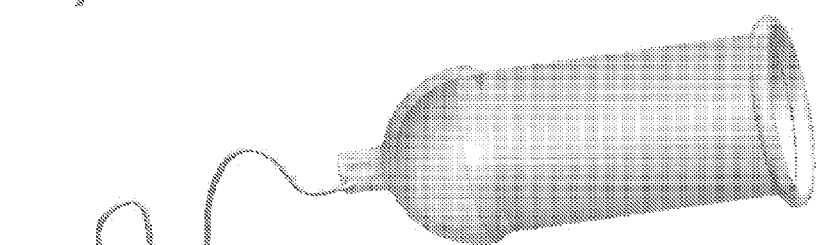
Figure 3:
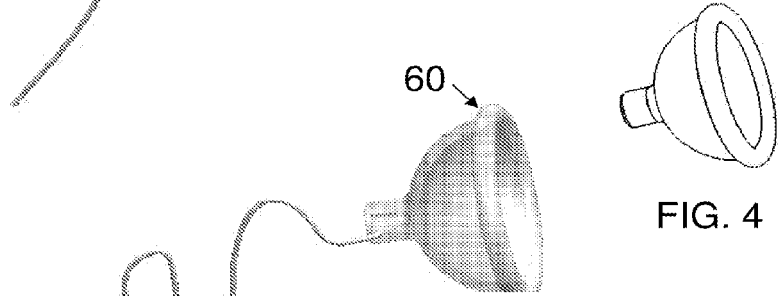

FIGS. 1-3 show an embodiment of a condom 10 for use in the present AI system. The condom includes a sheath 20 and a reinforced cup 30. The sheath and/or cup may be made of latex, silicone, neoprene, rubber, liquid silicone rubber (LSR), fluorosilicone (FVMQ), ethylene-propylene elastomers or other elastomeric materials.

Figure 4:
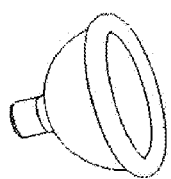
Figure 5:
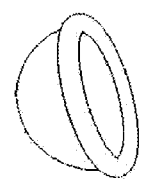
Figure 6:
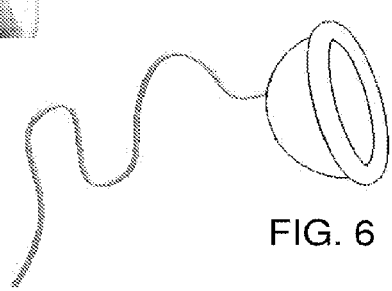

The cup may be made of material thicker or stiffer than that of the sheath to provide reinforcement. The reinforced cup caps one end of the sheath, so that the inner aspect of the cup forms an inner concave surface, and the outer aspect forms an outer convex surface. The inner concave surface may further have a distal recess where ejaculate can accumulate. The outer convex surface may or may not include a receptacle 40. A pull-string 50 may extend from the receptacle. The pull-string may be used to retrieve the condom after insemination. The sheath may be rolled up; FIG. 2 shows a partial rolling, and FIG. 3 shows a complete rolling. The rolled-up sheath forms a supporting ring 60 which further reinforces the cup. (Alternatively, the sheath may be detached from the cup.) FIG. 4 shows an embodiment lacking the pull-string. FIG. 5 shows an embodiment of a condom lacking the receptacle; FIG. 6 shows an embodiment of a condom in which a pull-string is attached directly to the convex outer surface.

Figure 7:
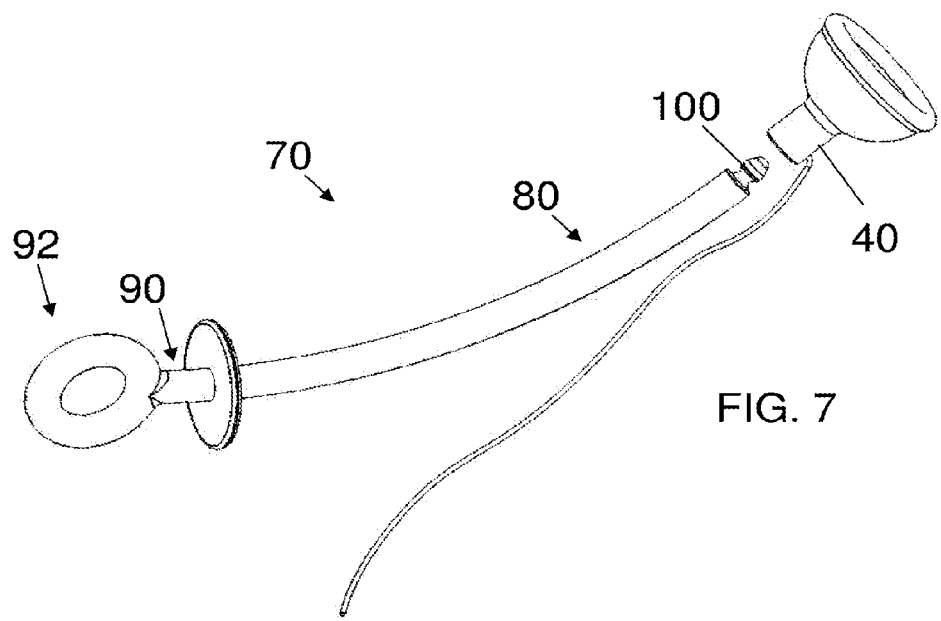
FIGS. 7-9 depict an exemplary embodiment of an artificial insemination system in two states.
Figure 8:
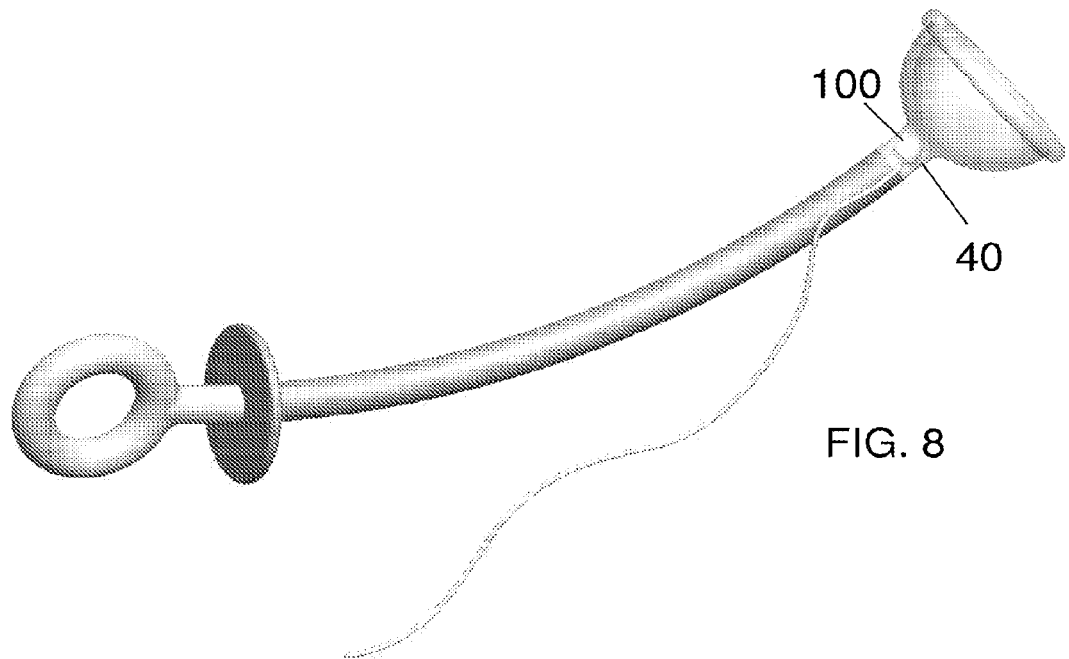
Figure 9:
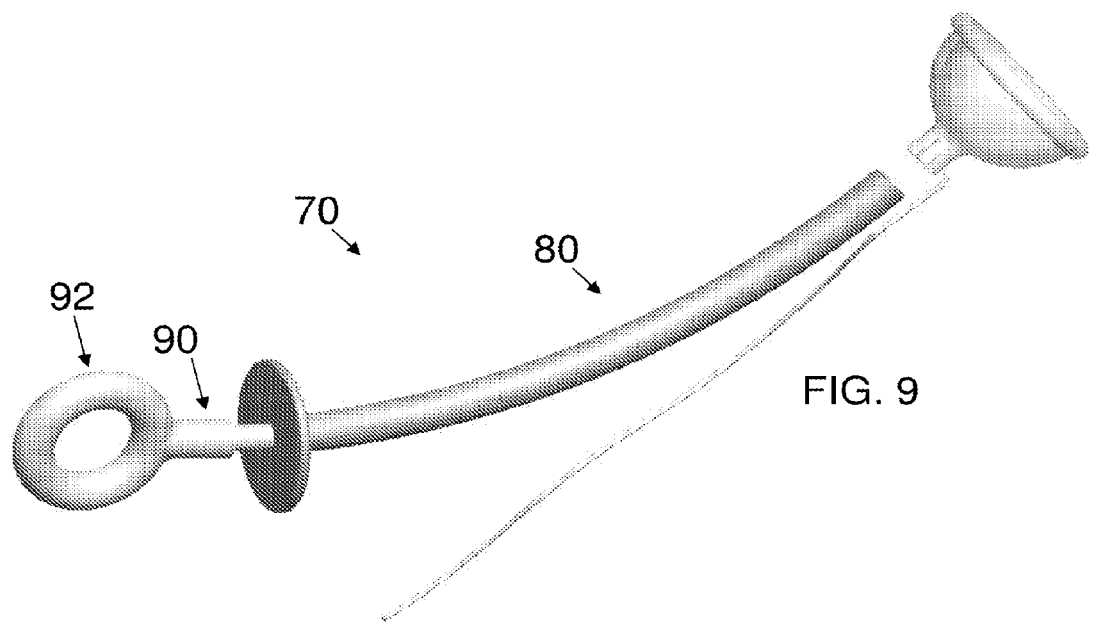

FIGS. 7-9 show the condom of FIGS. 1-3 with a delivery handle 70. The handle has an elongate extension that includes a sleeve 80 and plunger 90 which is slideable in the sleeve. The plunger may include a ring 92 or other feature that provides a purchase for a user to advance or retract the plunger relative to the sleeve. The condom attaches to the distal end of the delivery handle; as depicted, condom receptacle 40 receives a connector 100 on the distal end of the plunger with an interference fit, snap fit, or other fit separable locking feature sufficiently strong to keep the two parts attached during the advancement process. The sleeve is retracted relative to the plunger to expose the connector for attachment (FIG. 7); conversely, the sleeve is advanced to push the condom receptacle off the connector, as will typically be done once the condom has been positioned at a woman's cervix (FIG. 9). Although FIGS. 7-8 show the receptacle attaching to the plunger, it could also attach to the sleeve, and movement of the plunger would dislodge the condom from the sleeve. As shown, the connector is a peg, and the receptacle defines a bore. The peg and bore may be threaded, so that the handle and condom are attached or separated by twisting the parts relative to one another. Alternatively, they may form some other complementary pair, such as a luer lock, bayonet mount, and the like. The handle may be a single, monolithic piece in such an embodiment.

Figure 10:
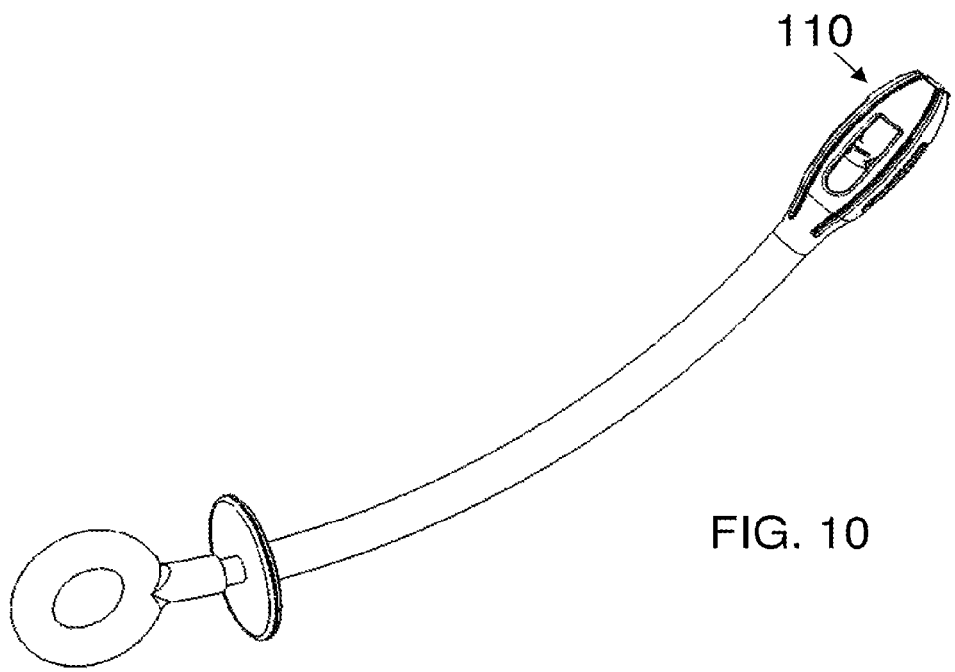
FIGS. 10-11 depict another exemplary embodiment of an artificial insemination system in two states.
Figure 11:
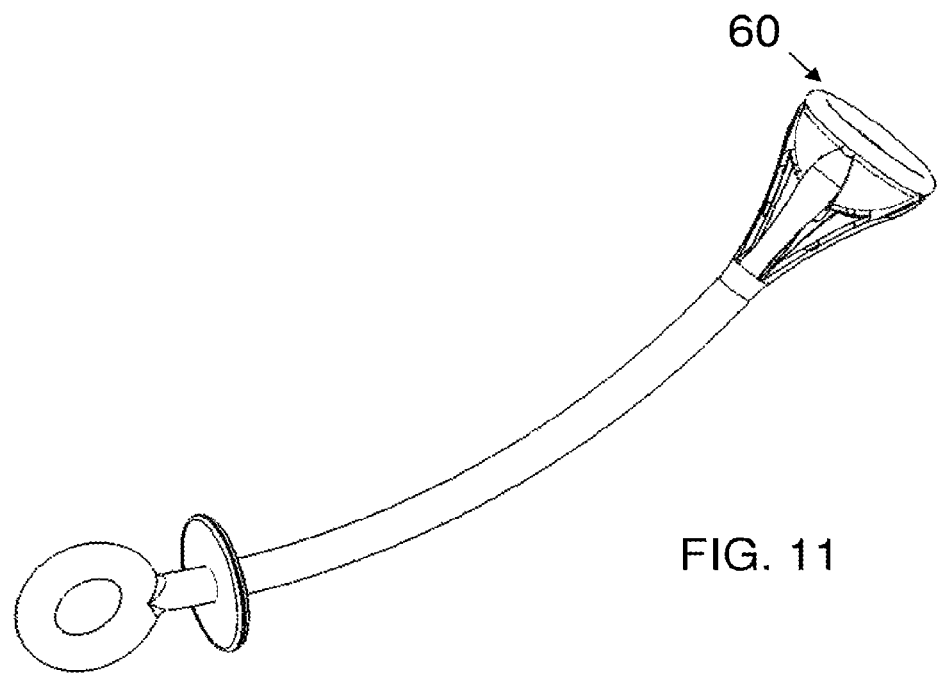

FIGS. 10-11 show another embodiment of an AI system in which the delivery handle's connector includes multiple fingers 110, which may be connected to one another or separate. Moving the plunger relative to the sleeve causes the fingers to open and close. In one orientation, the fingers are sufficiently open to receive and cradle the condom and/or receptacle and/or cup by contacting the outer convex surface; the condom and/or receptacle and/or cup may be supported on the fingers by its supporting ring 60. The fingers may be transitionable from a closed position (FIG. 10), which provides safety and/or helps to retain the semen in the receptacle when not in use, when being inserted into the vaginal tract, or when being withdrawn through the vaginal tract, and an attached position (FIG. 11), which cradles and supports the condom in delivery orientation and is open just enough to accommodate the cup of the condom but not the supporting ring. Alternatively, the attached position could be sufficiently open to accommodate the supporting ring as well.

Figure 12:
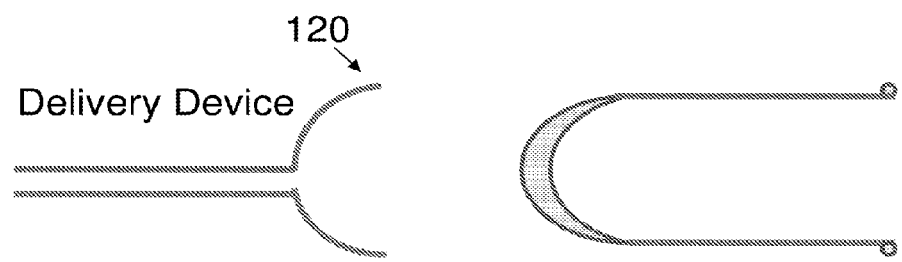
FIGS. 12-13 depict yet another exemplary embodiment of an artificial insemination system in two states.
Figure 13:
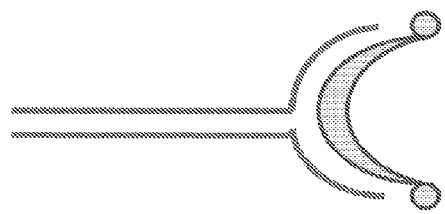
Figure 14:
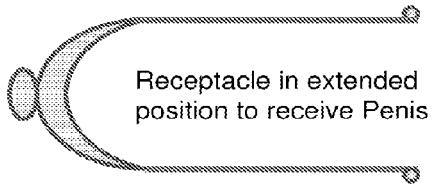
FIGS. 14-17 depict yet another exemplary embodiment of an artificial insemination system in four states.
Figure 15:
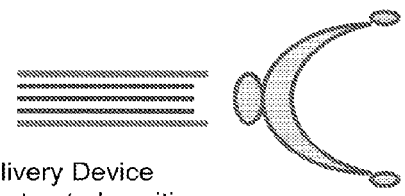
Figure 16:
Figure 17:

FIGS. 12-13 show another embodiment of an AI system in which the delivery device's distal end has a shape that complements the condom cup, such as a concave depression 120. The condom may rest in the delivery handle's depression. As shown in FIG. 10, the depression may be sized to receive the condom cup but not the supporting ring. The ring rests on the lip of the depression and helps to stabilize the condom. As above, the depression can be sized to accommodate the ring as well.

FIGS. 14-17 show another embodiment of an AI system in which the delivery handle includes multiple graspers 130, and the condom receptacle includes a protrusion 140. The graspers are biased to a closed position and are sized, shaped, and positioned to engage the protrusion.

The handle extension thus can attach to the cup's outer convex surface at the receptacle, and it may also attach at the edge.

The delivery handle may also include a detacher that is sized, shaped, and positioned to engage at least one of the connector and receptacle to detach them from one another.

Although the condom is described as having a "receptacle" and the handle a "connector," the handle may instead have a receptacle and the condom a connector.

Figure 18:
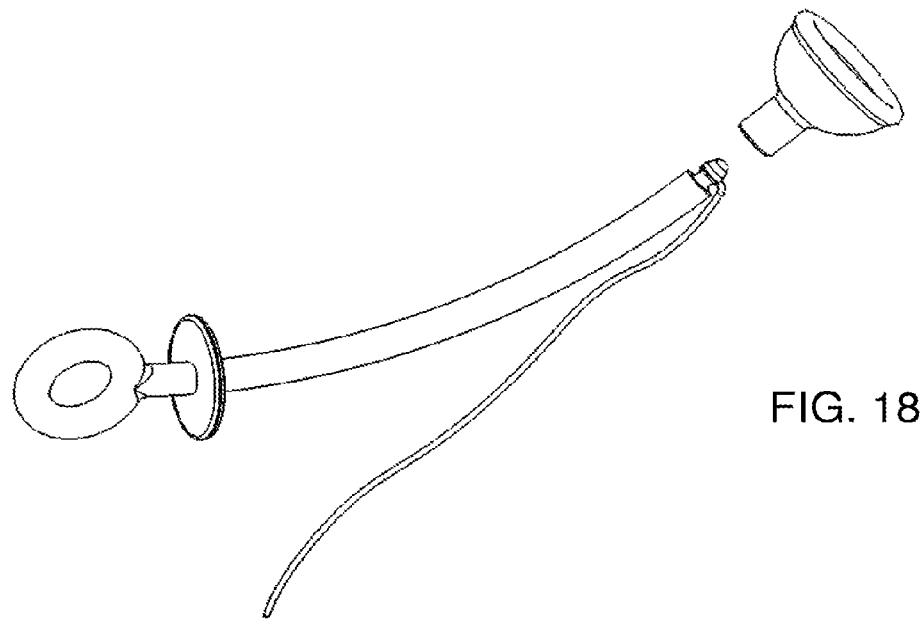
FIGS. 18-20 show an embodiment of an AI system in which a pull-string is transferred from the handle to the condom upon attachment of the two.
Figure 19:
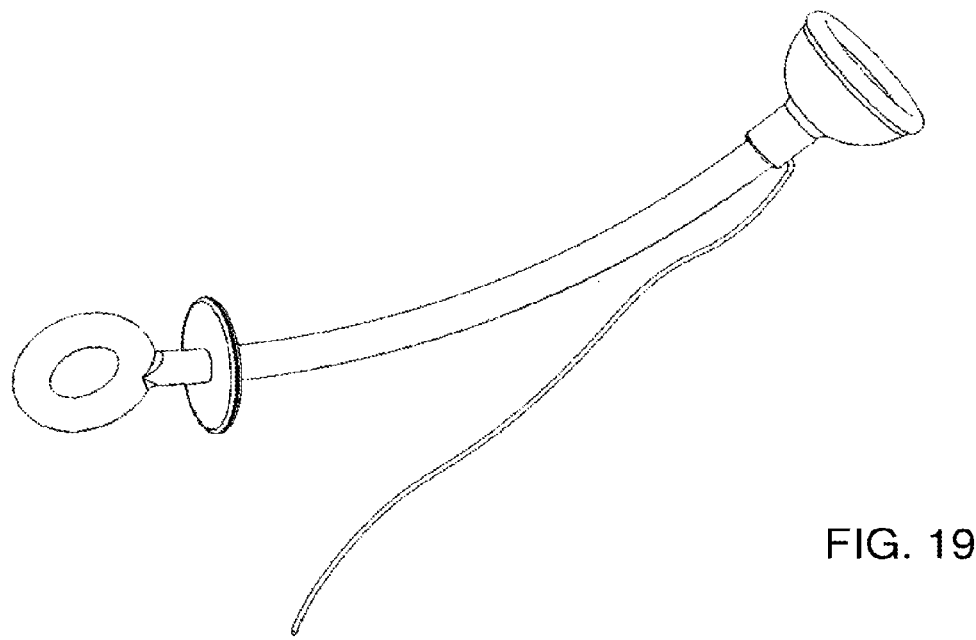
Figure 20:
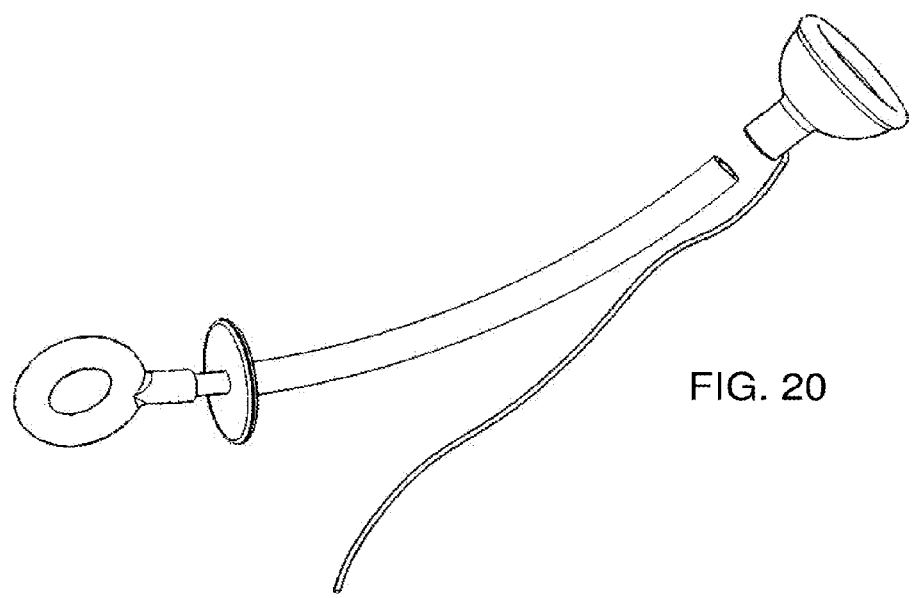

FIGS. 18-20 show an embodiment in which a pull-string initially attached to the delivery handle is transferred to the condom when the handle is attached to the condom. As the pull-string may interfere with sexual intercourse, it may be attached to the condom after removal from the penis and prior to advancement to the cervix. The pull-string may have a mechanical locking feature or adhesive on its distal end that will firmly attach when placed in apposition to the condom cup or receptacle (anywhere on the outer convex surface or supporting ring). Alternatively, the pull-string may be supplied initially attached to the sleeve 80 or plunger 90 than transferred to the condom receptacle 40 by either an interference or other fit so that the pull-string 50 would capture the receptacle 40 or concave surface of the condom 10 and stay attached to aid in removal of the condom cup from the cervix. Or the pull-string may be supplied by the sleeve or plunger and transferred to the condom by an anchor attachment to the distal end of the pull-string and embed into the receptacle 40 or concave surface of the condom 10. Or the pull-string may be supplied attached to a nub that may be attached to the condom's receptacle. The nub may be initially mounted on the delivery handle by a light interference fit or other retaining feature; when the delivery handle is attached to the condom receptacle, the nub makes contact with the receptacle and is seated in the receptacle with an interference or other mechanical retaining feature or adhesive that provides a stronger attachment to the cup than does the fit holding the nub to the handle, so that pulling away the handle leaves the nub, and pull-string, attached to the condom.

When using a condom that does not include a receptacle, a pull-string can be attached to the convex outer surface after intercourse and shortly before insertion for artificial insemination. Adhesive may be supplied that the user can apply to the pull-string and/or condom to attach the two. Alternatively, the pull-string and condom may be supplied with contact cement already applied so that the two parts will attach when touched together. The region of the condom carrying contact cement can be marked with an outline, or the cement can be differently-colored compared to the condom, to show the user where to apply the pull-string.

Figure 21:
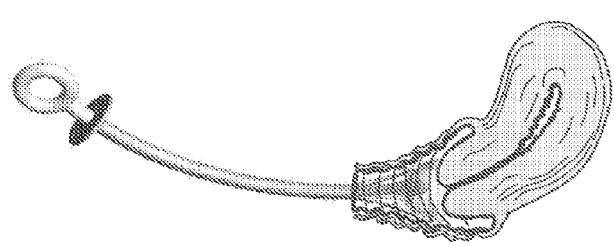
FIGS. 21-22 show an AI system in position at a cervix.
Figure 22:
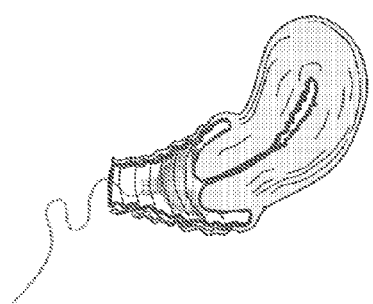

In use, a man wears the condom while having sexual intercourse, manually release, or other methods and ejaculates into the condom. The condom is removed from the penis, and the sheath is rolled down to the cup (or removed). The outer convex surface of the cup is attached to a delivery handle, which is then used to advance the cup, concave side distalmost, through the vaginal tract to the cervix. The cup is positioned near or on the cervix (FIGS. 21-22) and left in place for a period of time, typically 30 minutes to 7 hours, or 2-5 hours. The cup is then removed and discarded. The delivery handle may be left in place on the condom while the cup is kept in position at or on the cervix, or it may be removed. If the handle is to be kept in place, it may be permanently attachable to the condom to help ensure that the cup is easily removed. In such a case, the handle can be made of a soft and conforming material with enough column strength to support insertion. A pull-string should be attached to the convex outer surface of the cup if the delivery handle is to be removed.

In another embodiment, one member of the delivery handle (such as an inner, smaller cross-section member) is relatively soft and flexible and receives its support from the outer, rigid member of the handle. Then, once the inner member is attached to the cup, the rest of the delivery handle (the rigid portion) can be removed. The cup is then later removed using the flexible inner member. Alternatively, the rigid portion may be retained until the cup is positioned at the cervix (to provide support during insertion) and then removed (to avoid discomfort from prolonged presence in the vaginal tract).

The cup may be made of a bioresorbable material, so that it need not be removed after use.

The cup may be collapsible and sealable, such that it can be closed and sealed to itself after ejaculation until the user is ready for insertion, to provide a convenient way to store ejaculate temporarily. This feature also provides a method to help avoid spilling the semen out of the cup before it is positioned at the cervix.

The condom may also serve as an ergonomic cervical cap.

Figure 23:
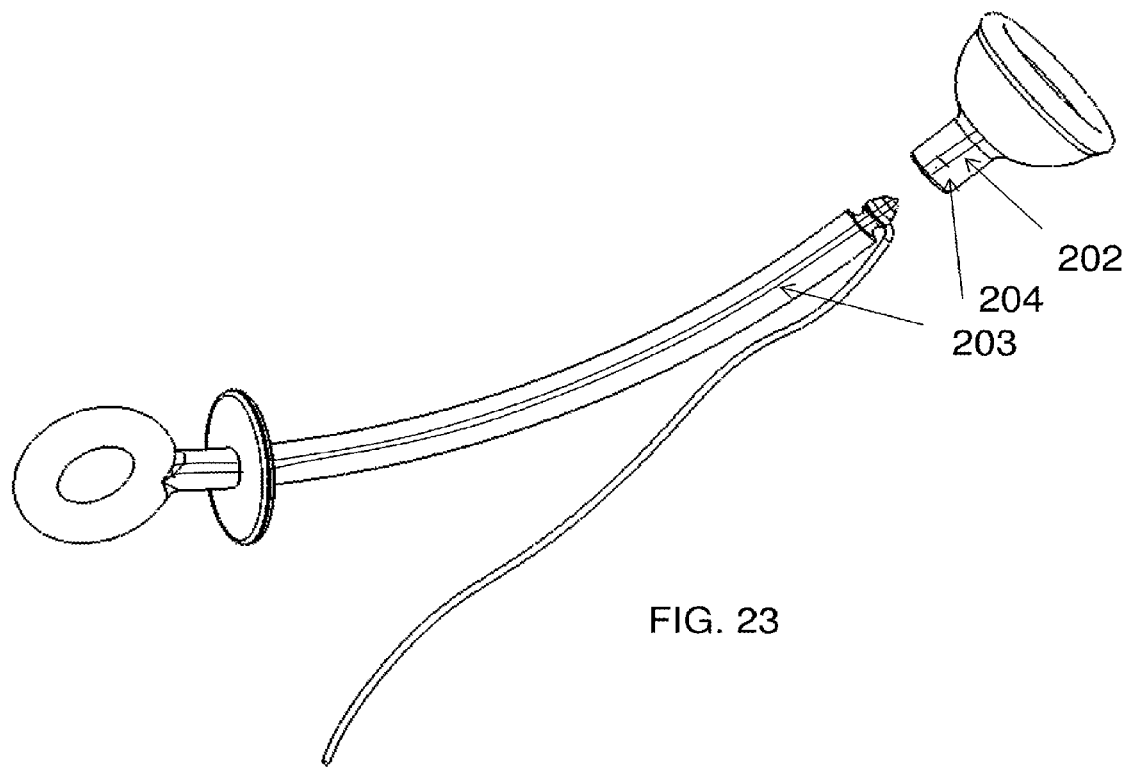
FIGS. 23-24 show an embodiment of an AI system for storage and delivery of a drug or other substance.
Figure 24:
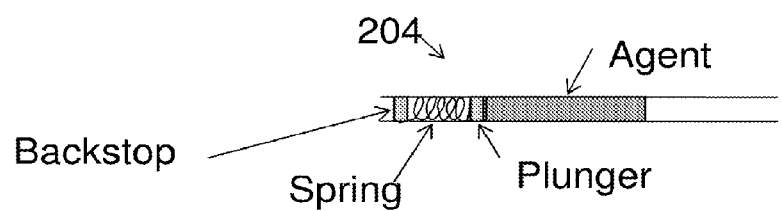

An introducer may also be provided to house, store, and/or deliver a lubricant, neutralizing agent, antibiotic, and/or sperm enhancer within the introducer to the vaginal tract. FIGS. 23-24 show an embodiment of a device that facilitates such storage and delivery. The delivery handle may have a channel 203 to deliver agents to the inner surface of the condom through a hollow channel 202 within the condom. This hollow channel 202 within the condom may or may not have a membrane or valve 204 within the channel that will be broken once the delivery handle has been inserted to allow the agent to pass into the concave surface of the condom.

The delivery of the agent, through the hollow channel, can be delivered with a syringe or through a valve 204 (one way valve, duckbill, etc.) within the delivery handle that delivers the agent to the concave surface of the condom. Delivery of agents can also be precoated on to the concave or convex surface of the condom or be added after collection of the ejaculate to the concave surface of the condom.

Figure 25:
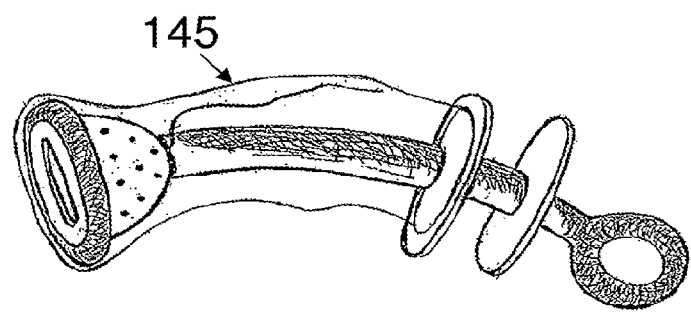
FIG. 25 shows an exemplary embodiment of an AI system with an over-sheath.

FIG. 25 shows an embodiment of a device that includes an over-sheath 145. The oversheath is added to the delivery handle once the delivery handle and the condom have been connected. The oversheath may be placed over the assembled delivery handle and condom to secure the ejaculate as well as ease advancement into the vaginal track. Once the device is properly located, the oversheath will be retracted to allow the final placement of the condom to the cervix. The oversheath may or may not have a perforation, a small hole, or weakness built into the sheath. This feature will readily come apart when the oversheath is tugged, thereby allowing easy retraction of the oversheath to uncover the condom. Use of the sheath can help prevent loss of ejaculate and ensure that as much as possible reaches the cervix with minimal interaction with the vaginal track.

Figure 26:
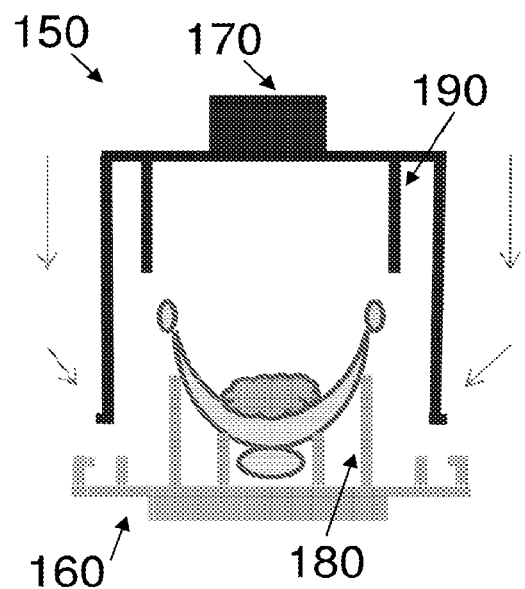
FIGS. 26-27 depict an embodiment of a specimen or semen storage system and an example of its use.
Figure 27:
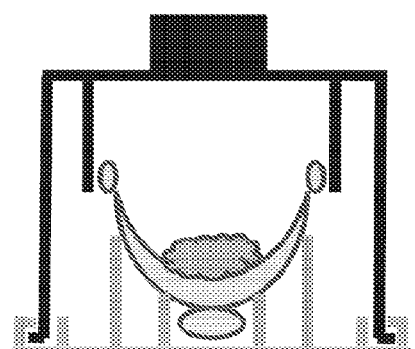

FIGS. 26-27 show an exemplary embodiment of a specimen storage system 150. After a specimen is received in the condom, the condom may be placed in a storage system for temporary storage, transport, preservation, and the like. The storage system may include a base 160 and a lid 170. The base may include a receiver for the condom, such as supports 180, a depression, fingers, graspers, or the like. The lid may include a seal 190 that engages the condom or the receiver to create a liquid-tight or air-tight seal for the specimen. The specimen may thereby be protected from loss and contamination. The lid and the base may engage one another with a lock, clamp, or other seal that eases handling, resists tampering, or will show evidence of tampering. The storage system may include a source of cold, such as an ice pack, an instant cold pack, such as an ammonium nitrate endothermic reaction pack, or a micro-refrigeration unit. The specimen storage system and or the condom could also have a proactive additive or coating that slows down or stops the breakdown of the ejaculate to optimize the sperms maintaining stasis during storage and or implantation.

Figure 28A:
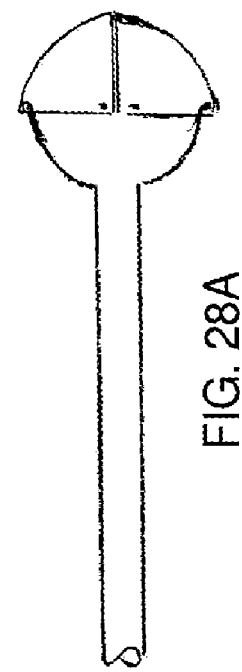
FIGS. 28A-F depict an embodiment of an artificial insemination system in six states.
Figure 28B:
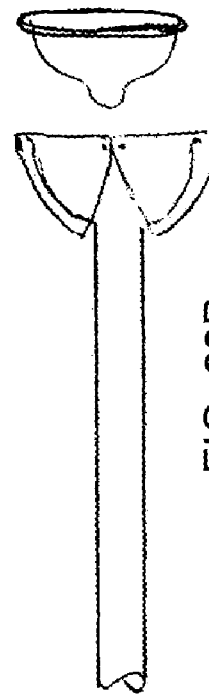
Figure 28C:
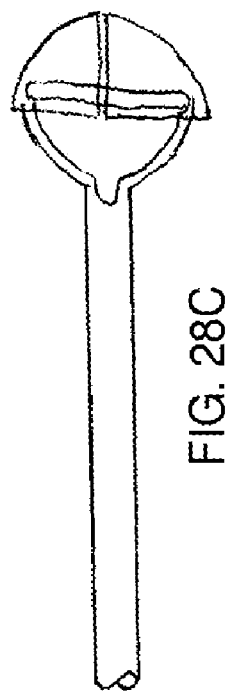
Figure 28D:
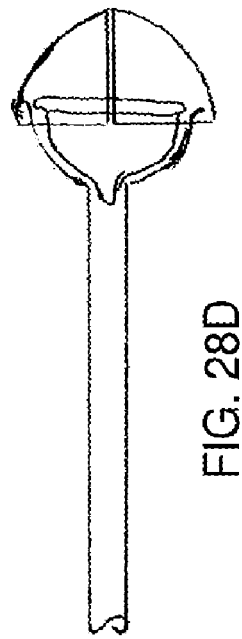
Figure 28E:
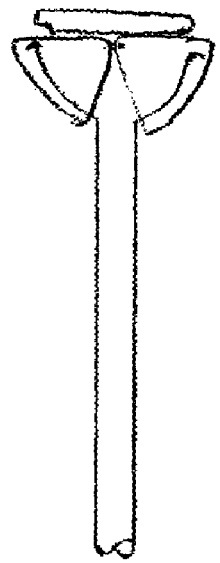
Figure 28F:
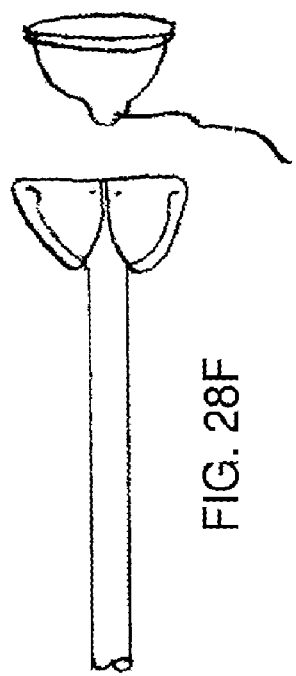
Figure 29A:
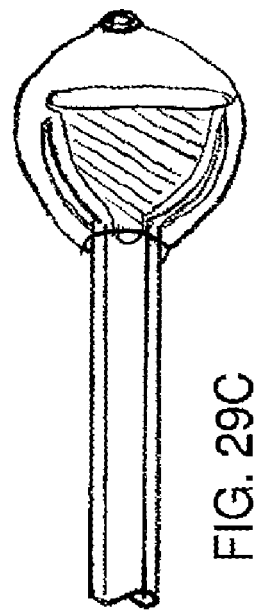
FIGS. 29A-D depict an embodiment of an artificial insemination system in four states.
Figure 29C:
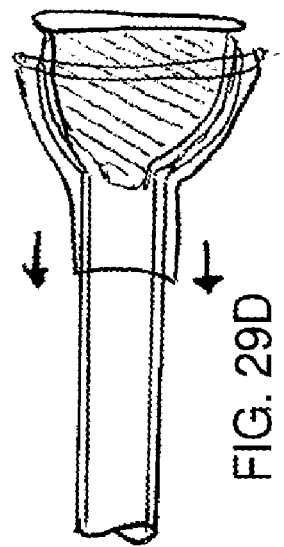
Figure 29B:
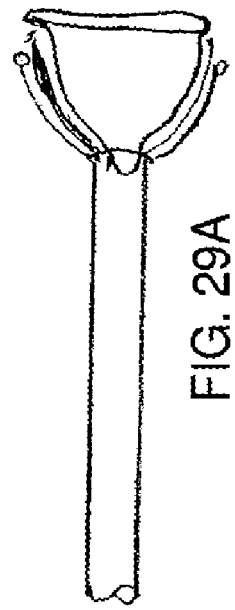
Figure 29D:
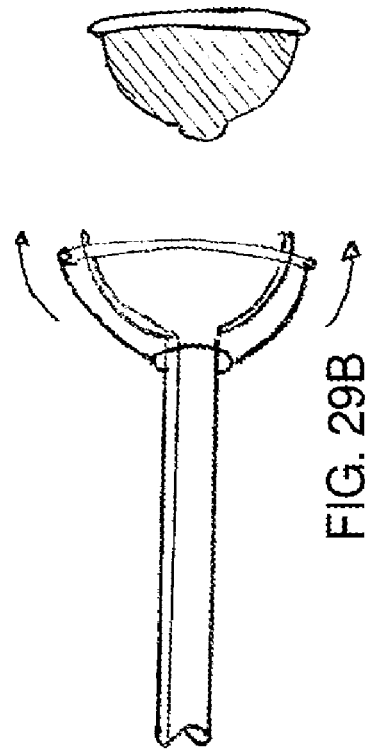

FIGS. 28A-F show an example of a system including a protection feature. The handle includes a mating surface (such as a concave depression as in FIGS. 12-13) and covers (FIG. 28A). The covers are opened to seat the collection device in the handle (FIG. 28B), closed (FIG. 28C-D), positioned for delivery and opened (FIG. 28E), so that the collection device is released (FIG. 28F).

FIGS. 29A-D show another system with a protection feature, which includes a sleeve threaded on the handle (FIG. 29A) that is pulled distally (FIG. 29B) to cover the collection device once it is seated in the handle (FIG. 29C) and then released (FIG. 29D) once the device is in position for release.

Figures 30A, 30B:
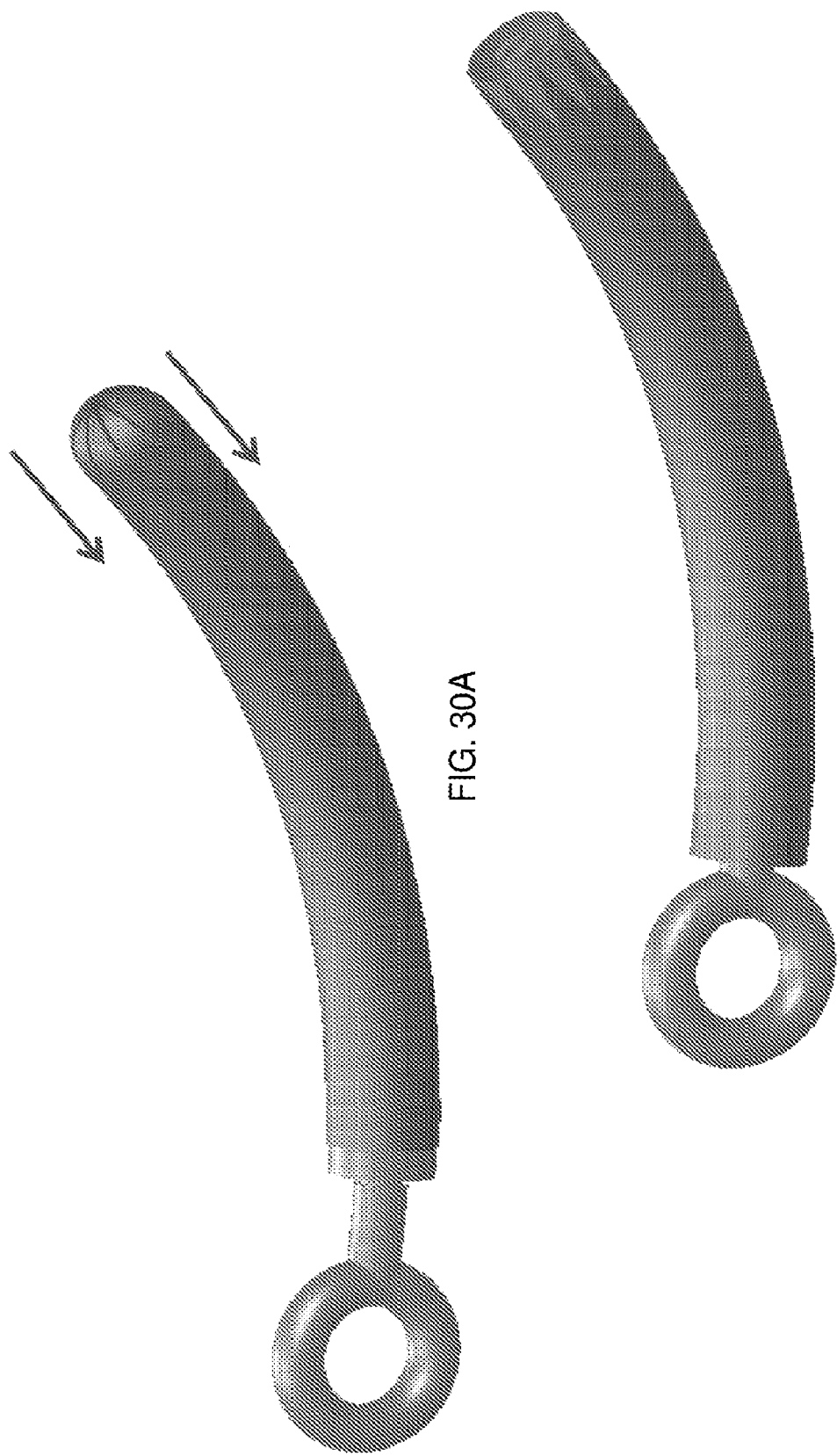
FIGS. 30A-B depict an embodiment of a handle to two states.
Figure 32C:
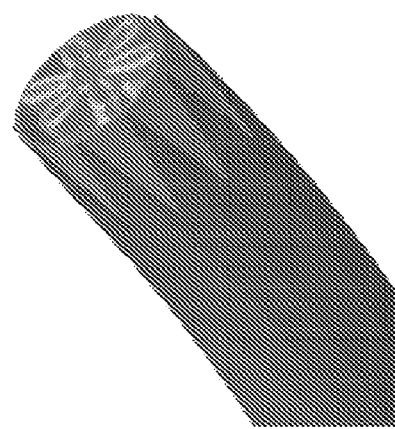
Figure 32B:
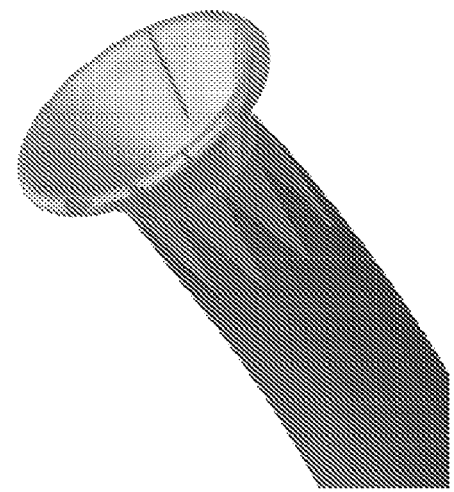
Figure 32D:
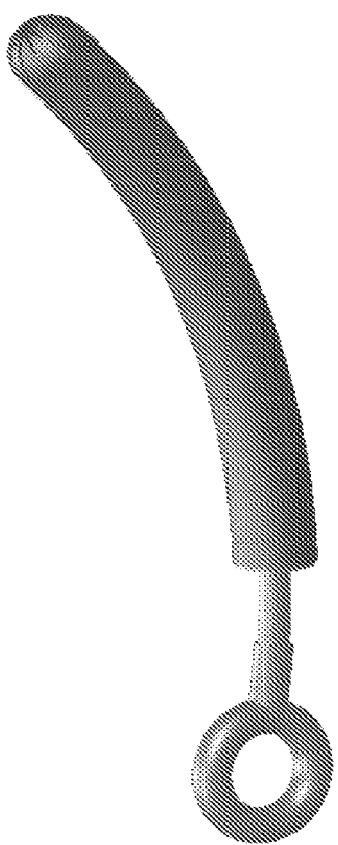
Figure 32A:
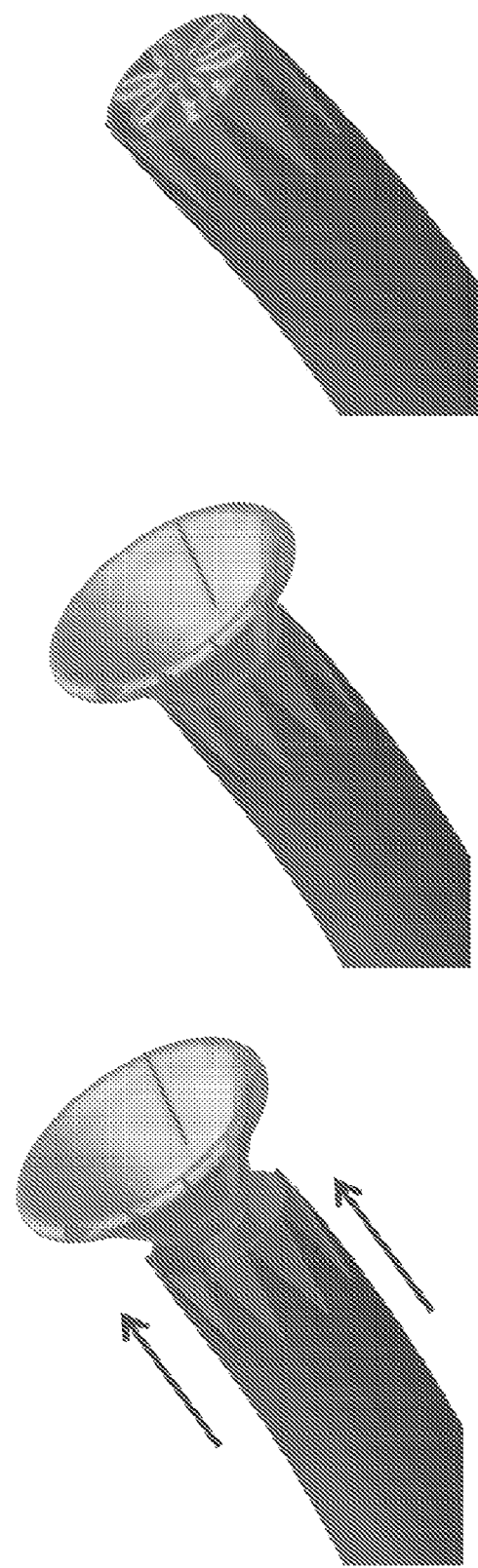

FIGS. 30A-B depicts a handle with a collar sheath that is perforated at its distal end so that is protects the distal end of the handle in a closed state (FIG. 30A) and separates to reveal contents of the handle when retracted (FIG. 30B).

FIG. 31A shows a schematic view of a condom. The condom includes weakened wall portions (such as thin webs, scores, folds, etc.) where the condom will preferentially fold when compressed as described below. The condom may also include a mounting feature at its proximal end for attachment to a receptacle in the handle (or vice versa).

FIGS. 31B-C, 32A-D, and 33A-D show the condom of FIG. 31A interacting with the handle. In FIGS. 31B-C, the condom (containing semen) is seated onto the handle. In FIGS. 32A-D, the collar is advanced distally (FIGS. 32A-B) to compress (FIG. 32C) and cover (FIG. 32D) the condom for safe delivery to the region of the cervix. Once delivered, the sheath is retracted (FIGS. 33A-B) to allow the condom to expand (FIG. 33C) and be released (FIG. 33D).

Figure 34B:
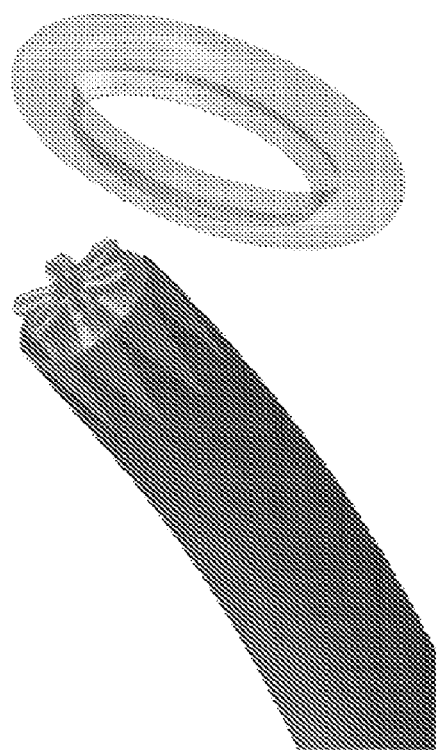
FIGS. 34A-B show an embodiment of a condom with a detachable sheath.
Figure 34A:
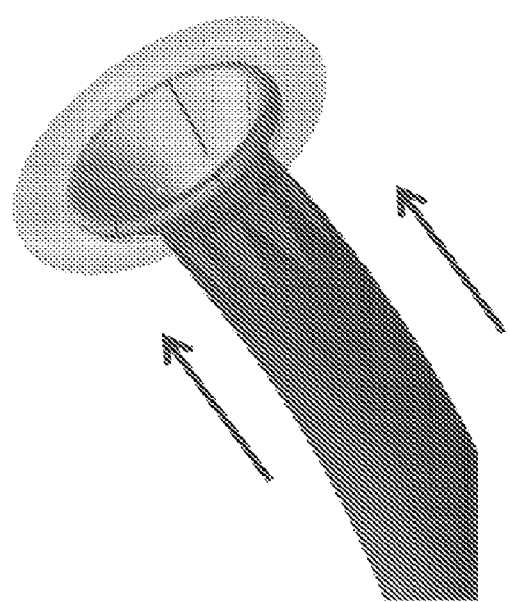

FIGS. 34A-B show an embodiment of a condom having a sheath that is detachable from the cup. In one embodiment, the act of distally sliding the handle collar urges the sheath to detach from the cup.

Figure 35C:
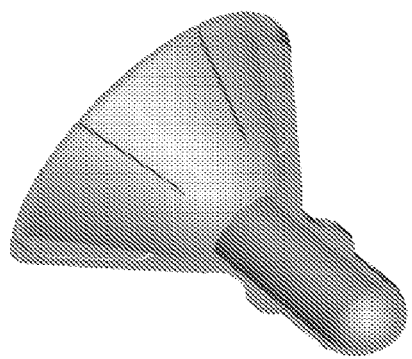
FIGS. 35A-C depict an embodiment of a condom with a reservoir.
Figure 35B:
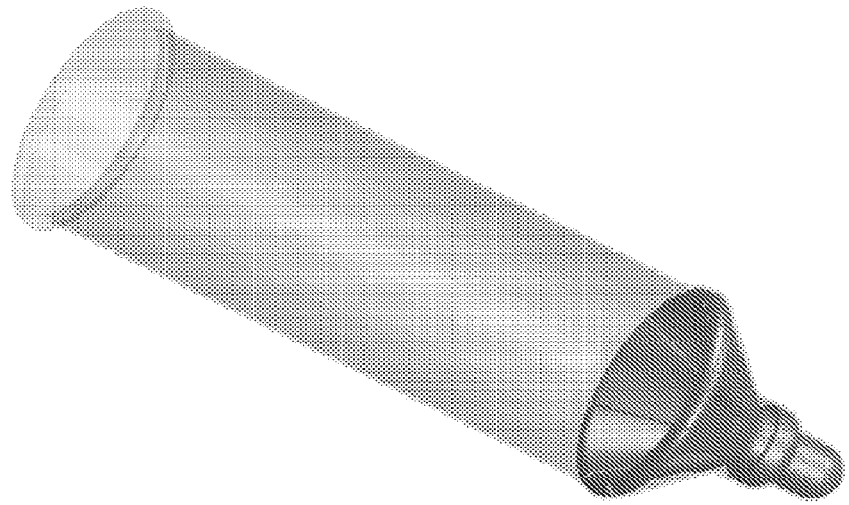
Figure 35A:
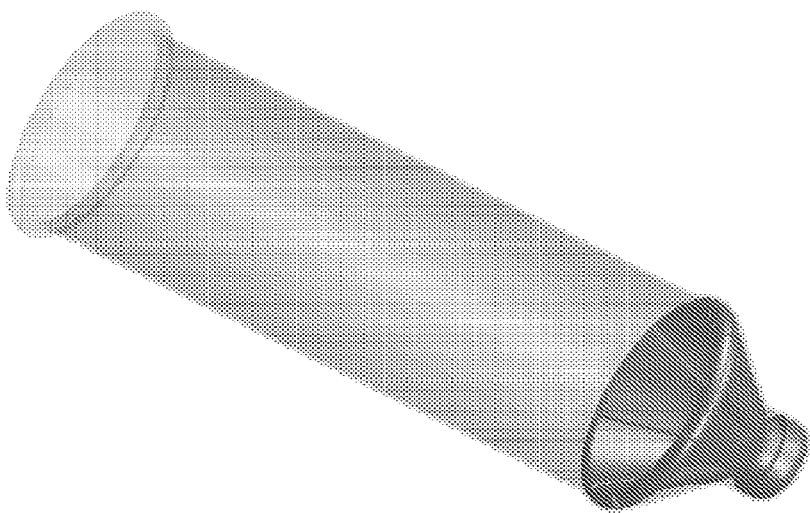
Figure 36C:
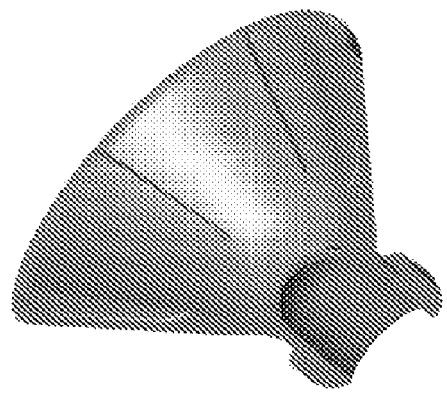
FIGS. 36A-C depict compression of the reservoir.
Figure 36B:
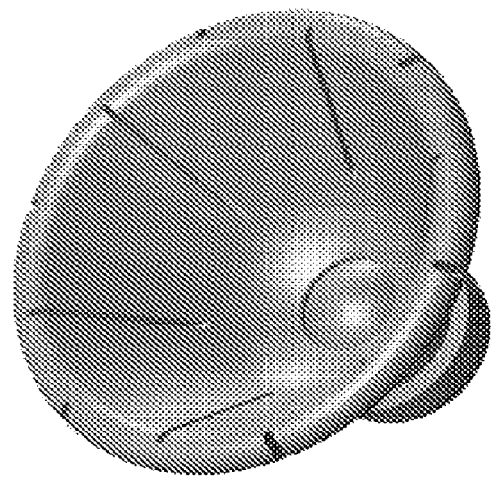
Figure 36A:
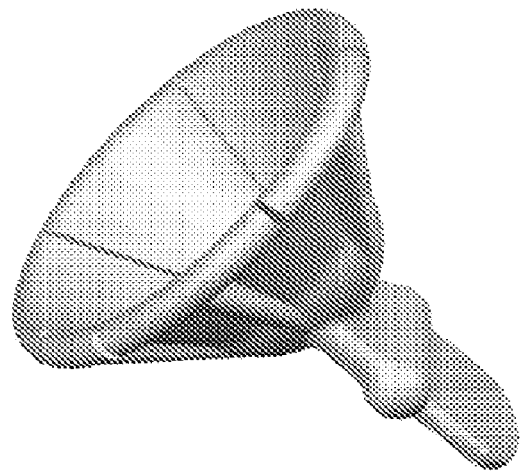

FIGS. 35A-C depict a condom having a reservoir. FIG. 35C shows the condom in cross-section. FIG. 35A shows the condom prior to ejaculation. The reservoir may be unexpanded in this state. Ejaculate is propelled to the distal tip of the condom, thereby causing the reservoir to expand and receive the ejaculate (FIG. 35B). Delivery of semen from this condom is facilitated by compressing the reservoir, thereby propelling the semen out of the cup. As shown in FIG. 36A, compression may be accomplished simply by flattening the reservoir in one or more dimensions. As shown in FIGS. 36B-C, the reservoir also can be inverted to accomplish the same thing.

Figures 37A, 37B:
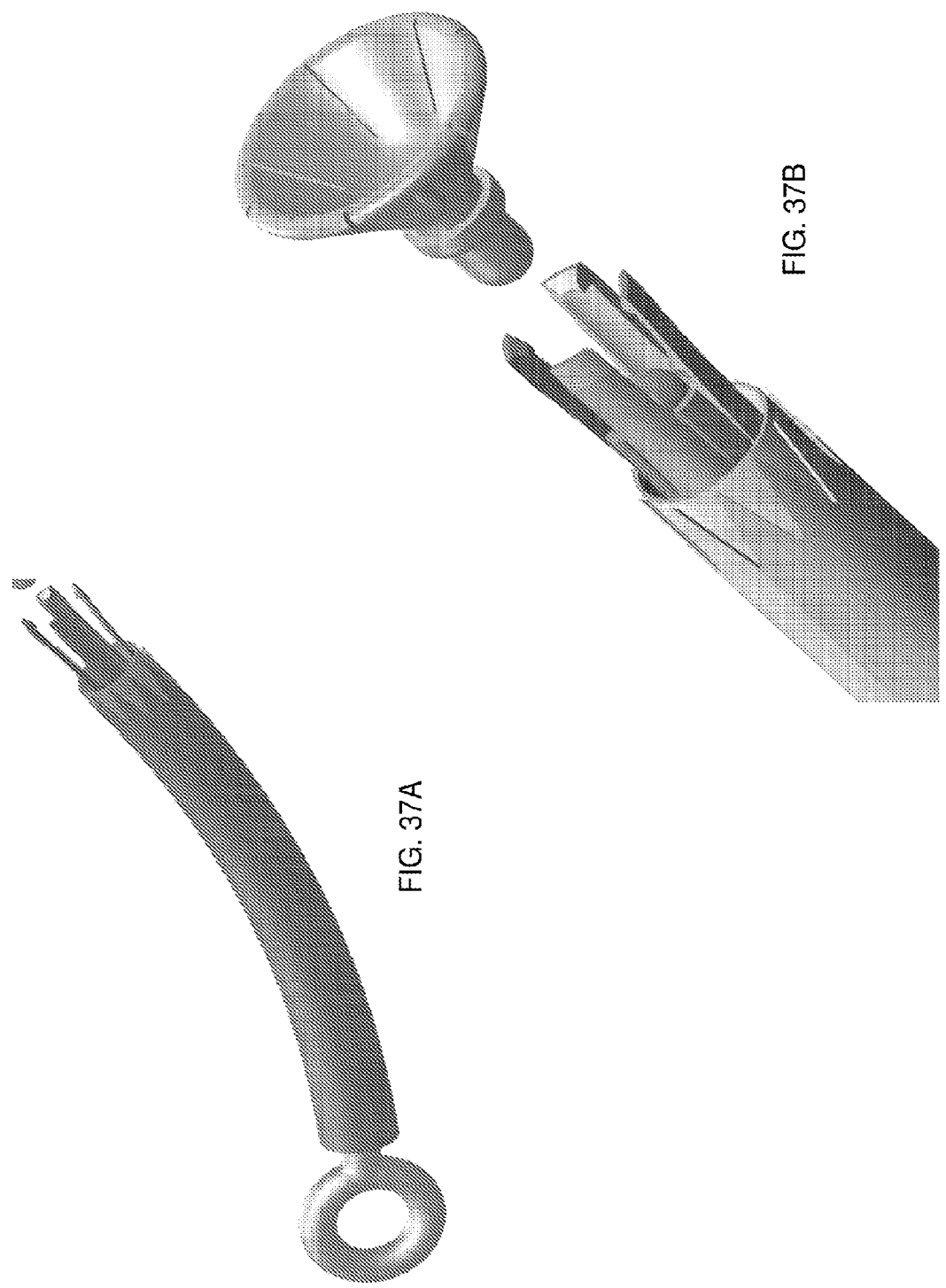

FIGS. 37A-B, 38A-G, 39A-E, 40A-C, and 41A-B depict the reservoir condom in use with a handle. The handle has graspers or retaining clips (FIG. 37A) or some other structure to hold the condom (FIG. 37B). As described earlier, the handle collar may be advanced to compress and protect the condom (FIGS. 38A-G). But when the condom is later ejected (FIGS. 39A-G), the reservoir is inverted during ejection, providing extra propulsion for the semen. FIGS. 40A-C show that inside the handle is a reservoir inverter. When a plunger is advanced (FIG. 40B), the inverter is pressed against the reservoir and causes it to invert from a convex to a concave state as the condom is pushed out of the handle.

FIGS. 38G, 39A-G, 40A-C, and 41A-B also depict attaching a pull-string to the condom. The pull-string is attached to the reservoir inverter. As the plunger is advanced and the reservoir inverter inverts the reservoir, a retaining feature (a mating connector and receptacle pair, one of which is on the inverter and the other of which is on the condom) secures the reservoir inverter to the condom, thereby also securing the string relative to the condom (FIG. 39E). The retaining feature may be reversible or irreversible. The pull-string can then be used to retrieve the device, as discussed earlier.

FIGS. 42A-D and 43A-B depict a semen storage system. If freshly ejaculated semen is not to be used immediately, it may be stored in the storage system. The semen-containing condom may be rolled onto the storage device (FIGS. 42A-C) for storage. When artificial insemination is to be performed, the storage device (with semen-containing condom) is positioned against a handle with a new condom mounted on it (FIG. 42D). Depressing a first plunger (FIG. 43A) causes the storage condom to be pierced, and depressing a second plunger (FIG. 43B) (or further depressing the first plunger), causes a pusher to push the collected semen out of the ruptured storage condom into the delivery condom. The handle and delivery condom are omitted from FIGS. 43A-B for clarity.

I claim:

1. An artificial insemination device comprising:
   a condom comprising:
      a sheath; and
      a reinforced cup that caps one end of the sheath, thereby having an inner concave surface and an outer convex surface;
   a delivery handle comprising an elongate extension sized and shaped to contact the outer convex surface of the condom cup; and
   a pull-string attachable to the outer convex surface of the condom;
   wherein the device is transitionable from:

(a) a first state in which the pull-string is attached to the handle and not attached to the outer convex surface of the condom;

to (b) a second state in which the pull-string is not attached to the handle and is attached to the outer convex surface of the condom.

2. The device of claim 1, wherein the delivery handle comprises a connector at a distal end of the elongate extension, and the outer convex surface of the condom cup comprises a receptacle sized and shaped to attach releasably to the connector.

3. The device of claim 2, wherein the receptacle comprises a protrusion, and the connector comprises biased graspers sized, shaped, and positioned to engage the protrusion.

4. The device of claim 2, further comprising a nub to which the pull-string is attached.

5. The device of claim 4, wherein in the first state, the nub is mounted on the delivery handle by a light interference fit, and in the second state, the nub is seated in the receptacle with an interference fit that provides a stronger attachment to the cup than that the light interference fit provides to the delivery handle.

6. The device of claim 1, wherein the elongate extension comprises a cradle sized and shaped to engage the outer convex surface of the condom cup.

7. The device of claim 1, wherein the delivery handle releasably contacts the outer convex surface of the condom cup.

8. The device of claim 1, wherein the cup defines an orifice which is in fluid communication with a channel of the elongate extension when the cup and extension contact one another.

9. The device of claim 8, wherein a one-way valve permits flow into, but not out of, the cup.

10. The device of claim 8, wherein the elongate extension channel contains a substance for introduction into the cup.

11. The device of claim 10, wherein the elongate extension further comprises a plunger positioned to advance the substance from the channel into the cup.

12. The device of claim 1, wherein the condom further comprises a deformable reservoir in the cup.

13. The device of claim 12, wherein the delivery handle further comprises a reservoir inverter shaped to invert the deformable reservoir as the inverter is advanced relative to the condom, thereby expelling contents of the condom cup.

14. The device of claim 13, wherein the pull-string is attached to the reservoir inverter.

15. The device of claim 14, wherein the reservoir inverter and the condom each comprise one of a connector and a receptacle, which are sized and shaped to attach to one another, thereby holding the reservoir inverter to the condom.

16. An artificial insemination method comprising:
causing semen to be ejaculated into the cup of the condom of the device of claim 1; then
rolling the sheath of the condom down to the cup to form a supporting ring for the cup;
contacting the outer convex surface of the cup to the elongate extension of the delivery handle;
advancing the cup and elongate extension to a cervix so that the ejaculate faces the cervix;
retrieving the cup after a delay.

17. The method of claim 16, further comprising withdrawing the elongate extension while leaving the cup at the cervix.

18. The method of claim 17, further comprising:
attaching a string to the condom before advancing; and
wherein retrieving comprises pulling the string.

19. The device of claim 1, wherein the delivery handle comprises:
a connector at a distal end of the elongate extension, and the connector comprises fingers sized and shaped to receive the condom; and
a plunger operably connected to the fingers such that sliding the plunger causes the fingers to open and close.

20. The device of claim 19, wherein the condom is supported on the fingers by a supporting ring formed by rolling the sheath down to the cup.

21. The device of claim 19, wherein the fingers open enough to accommodate the cup of the condom but not a supporting ring of the condom formed by rolling the sheath down to the cup.

22. The device of claim 19, wherein the condom further comprises a deformable reservoir in the cup.

23. The device of claim 22, wherein the delivery handle further comprises a reservoir inverter shaped to invert the deformable reservoir as the inverter is advanced relative to the condom, thereby expelling contents of the condom cup.

24. The device of claim 23, wherein the pull-string is attached to the reservoir inverter.

25. The device of claim 24, wherein the reservoir inverter and the condom each comprise one of a connector and a receptacle, which are sized and shaped to attach to one another, thereby holding the reservoir inverter to the condom.

26. The device of claim 1, wherein the pull-string is attached directly to the convex outer surface.

27. The device of claim 1, wherein the pull-string comprises a distal end and a mechanical locking feature on the distal end.

28. The device of claim 1, wherein the pull-string comprises a distal end and an adhesive or contact cement applied thereon.

* * * * *

UNITED STATES PATENT AND TRADEMARK OFFICE
CERTIFICATE OF CORRECTION

PATENT NO. : 8,192,347 B2  
APPLICATION NO. : 13/039568  
DATED : June 5, 2012  
INVENTOR(S) : Stephen A. Bollinger It is certified that error appears in the above-identified patent and that said Letters Patent is hereby corrected as shown below:

On the Title page, Item (63), left col., Related U.S. Application Data: change "May 18, 2002" to --May 18, 2009--

Signed and Sealed this
Fourteenth Day of August, 2012

David J. Kappos
*Director of the United States Patent and Trademark Office*

UNITED STATES PATENT AND TRADEMARK OFFICE
CERTIFICATE OF CORRECTION

PATENT NO.        : 8,192,347 B2                                    Page 1 of 1
APPLICATION NO.   : 13/039568
DATED             : June 5, 2012
INVENTOR(S)       : Bollinger et al.

It is certified that error appears in the above-identified patent and that said Letters Patent is hereby corrected as shown below:

Title Page, Item (75) Inventor is corrected to read:
-- Stephen August Bollinger, Mansfield (MA);
   Glenn Kanner, Monroeville (PA); --.

Signed and Sealed this
Fifteenth Day of September, 2015

Michelle K. Lee
*Director of the United States Patent and Trademark Office*